United States Patent [19]

Phillips

[11] Patent Number: 4,621,929

[45] Date of Patent: Nov. 11, 1986

[54] FIBER OPTIC THERMAL ANEMOMETER

[75] Inventor: Stephen R. Phillips, Walnut Creek, Calif.

[73] Assignee: Luxtron Corporation, Mountain View, Calif.

[21] Appl. No.: 541,384

[22] Filed: Oct. 12, 1983

[51] Int. Cl.[4] .................. G01N 25/20; G01J 5/48
[52] U.S. Cl. ...................... 374/43; 374/131;
374/20; 374/141; 73/295; 73/861.05;
73/861.22; 73/714; 356/44
[58] Field of Search ................ 374/43, 44, 45, 54,
374/130, 131, 141, 142, 143, 164, 17–20;
356/43, 44; 250/458.1, 461.1, 337, 227, 356.1,
357.1, 361 R; 73/861.05, 861.22, 292, 295, 700,
714; 219/553, 10.55 R, 10.55 A; 34/4; 165/154,
155

[56] References Cited

U.S. PATENT DOCUMENTS

| | | | |
|---|---|---|---|
| 673,075 | 4/1901 | Douane | 165/154 |
| 3,251,228 | 5/1966 | Hanebuth | 73/700 |
| 3,580,081 | 5/1971 | Greenberg et al. | 73/399 |
| 3,797,310 | 3/1974 | Babcock et al. | 73/295 |
| 3,917,945 | 11/1975 | Sema et al. | 250/356.1 |
| 4,016,761 | 4/1977 | Rozzell et al. | 250/227 |
| 4,075,493 | 2/1978 | Wickersheim | 374/131 |
| 4,136,566 | 1/1979 | Christensen | 73/356 |
| 4,140,393 | 2/1979 | Cetas . | |
| 4,179,927 | 12/1979 | Saaski | 73/350 |
| 4,204,119 | 5/1980 | Yasuno et al. | 250/337 |
| 4,215,275 | 7/1980 | Wickersheim | 356/44 |
| 4,223,226 | 9/1980 | Quick et al. | 250/458 |
| 4,245,507 | 2/1985 | Samulski | 374/131 |
| 4,295,739 | 10/1981 | Meltz et al. | 356/43 |
| 4,313,344 | 2/1982 | Brogardh et al. | 374/131 |
| 4,320,650 | 3/1982 | Kita | 73/861.22 |
| 4,344,315 | 8/1982 | Moxon et al. | 374/44 |
| 4,344,322 | 8/1982 | Plapp | 73/118 |

(List continued on next page.)

FOREIGN PATENT DOCUMENTS 0085875 8/1983 European Pat. Off. .
2445804 4/1976 Fed. Rep. of Germany .
2113837 8/1983 United Kingdom .

OTHER PUBLICATIONS

Freymuth, P. "Feedback Control Theory for Constant Temperature Hot-Wire Anemometers", *The Rev. of Sci. Instrum.*, vol. 38, No. 5, pp. 677–681, 1967.

Schultz, D. L. et al., "Velocity Distribution and Transition in the Arterial System", Wolstenholme and Knight (eds) *Circulatory and Respiratory Mass Transport*, published by Little, Brown and Co., Boston, 1969, pp. 172–202.

(List continued on next page.)

*Primary Examiner*—Charles Frankfort
*Assistant Examiner*—Patrick R. Scanlon
*Attorney, Agent, or Firm*—Majestic, Gallagher, Parsons & Siebert

[57] ABSTRACT

To measure the heat transfer coefficient of a sample, an element with temperature sensitive optical properties is placed in contact or implanted in the sample. The element is heated or cooled. The temperature difference between the element and the unheated sample and the rate of heating or cooling indicate the heat transfer coefficient of the sample. In one embodiment, the element is heated or cooled at a constant rate. The heat transfer coefficient of the sample is then inversely related to the difference in temperature between the element and the unheated sample. Alternatively, the element may be heated or cooled at such a rate that the temperature difference between the element and the unheated sample remains substantially constant. The heat transfer coefficient of the sample then varies directly with the rate of heating or cooling. The heat transfer coefficient of a sample is a measure of its composition and other physical properties. The composition of gasses, liquids, the presence of bubbles in a liquid, and fluid levels can be detected by the optical technique. Pressure and flow rates of fluids can also be detected. The technique can be used also to more accurately measure the thermal conductivity and temperature of small objects with small heat capacities.

79 Claims, 30 Drawing Figures

| | | |
|---|---|---|
| 4,345,482 | 8/1982 | Adolfsson et al. ............... 73/862.59 |
| 4,355,910 | 10/1982 | Quick et al. ......................... 374/162 |
| 4,357,106 | 11/1982 | Tschirren et al. .................... 356/44 |
| 4,362,057 | 12/1982 | Gottlieb et al. ......................... 374/4 |
| 4,373,768 | 2/1983 | Clarke ............................... 350/96.34 |
| 4,374,328 | 2/1983 | Tekippe et al. .................. 250/458.1 |
| 4,376,890 | 3/1983 | Engstrom et al. ................... 250/227 |
| 4,384,484 | 5/1983 | Kohama et al. ....................... 73/204 |
| 4,403,143 | 9/1983 | Walker et al. ....................... 250/227 |
| 4,417,140 | 11/1984 | Adolfsson et al. .................. 250/227 |
| 4,435,978 | 3/1984 | Glatz ..................................... 73/155 |
| 4,448,547 | 5/1984 | Wickersheim ...................... 374/131 |
| 4,458,709 | 7/1984 | Springer .......................... 73/861.05 |

OTHER PUBLICATIONS

*Mark's Standard Handbook for Mechanical Engineers,* 7th Ed., McGraw-Hill, N.Y. 1967, pp. 4-90-4-100.

Seed, W. A. and Wood, N. B. "Development and Evaluation of Hot-Film Velocity Probe for Cardiovascular Studies" *Cardiovascular Research,* vol. 4, pp. 253-1970.

Brooks Mass Flow Bulletin B-5800, Brooks Instrument Division, Emerson Electric Co.

Varian Vacuum Gauge Manual Operating Instructions for Varian Model 810 and 810-2 Thermocouple Vacuum Gauge Controller, Varian/Lexington Vacuum Div., Lexington, Mass.

Bestion, D. et al., "Comparison Between Constant-Current and Constant-Temperature Hot-Wire Anemometers in High-Speed Flows", *The Rev. Sci. Instrum.,* vol. 54, No. 11, pp. 1513-1524, Nov. 1983.

Freymuth, P. "A Bibliography of Thermal Anemometry", published by TSI Incorporated 1982.

TSI Incorporated Catalog 1983, "Hot Wire/Hot Film Anemometry Probes and Accessories".

NASA Tech Briefs "Measuring the Liquid Content of a Gas", vol. 8, No. 4, p. 525.

INTEK Bulletin 880 "Thermal Flow Rate Instruments and Flow Switches" Intek Inc., Columbus, Ohio.

Clark, C. and Schultz, D. L. "Velocity Distribution in Aortic Flow" *Cardiovascular Research,* vol. 7, pp. 601-613, 1973.

TSI Technical Bulletin No. 20 "TSI Split Film Sensor Calibration and Application", Thermo-Systems Inc., St. Paul. Minn.

Milner, C. J. "Fast, Thermostatic, Pirani Gauge" *Rev. Sci. Instrum.,* vol. 54, No. 7, pp. 890-893, Jul. 1983.

ZI-TECK Catalog AVM500 Series Air Velocity Meters Z-Teck Division, Aikenwood Corp., Palo Alto, Calif.

Cheng, A. F. "The Story of Fluoroptic Thermometry", Luxtron Corp. Technical Information Paper, Mountain View, Calif.

Wickersheim, K. A., et al., "Optical Temperature Measurement", *Industrial Research/Development,* Dec. 1979.

Ovren, C. et al., "Fiber-Optic System for Temperature and Vibration Measurements in Industrial Applications" *Optics and Lasers in Engineering,* vol. 5, pp. 155-172, 1984.

Mellberg, R. S. "Fiber-Optic Sensors" *SRI Internatinal Research Report* No. 684, Summer 1983.

Harmer, A. L. "Principles of Optical Fibre Sensors and Instrumentaion" *Measurement and Control,* vol. 15, pp. 143-151, Apr. 1982.

Kyuma, K., et al., "Development of Fibre Optic Sensing System-A Review", *Optics and Letters in Engineering,* vol. 3, pp. 155-182, 1982.

Hirschfeld, T., et al., "Fiber Optics Temperature and Pressure Probe" W. S. Lyon Editor), Analytical Spectroscopy, Elsevier Science Publishers B.V., Amsterdam 1984.

Sandberg, Chet and Gerling, John "Fluoroptic Thermometery TM a New Tool for Temperature Measurement in Severe Electro-Magnetic Environment" *ASME paper 84-HT-50,* 1983.

Omega 1984 Handbook, *Temperature Measurement Handbook and Encyclopedia.*

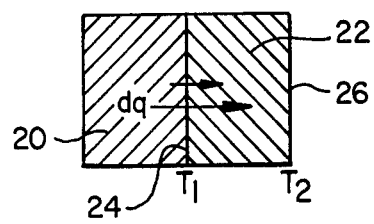
FIG._1.
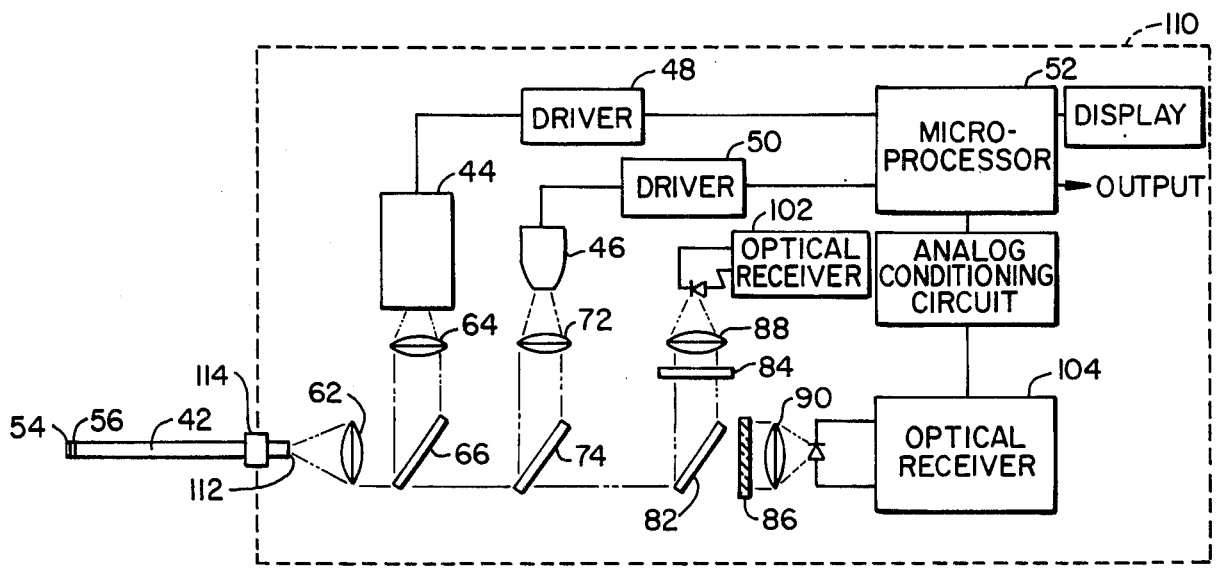
FIG._2.
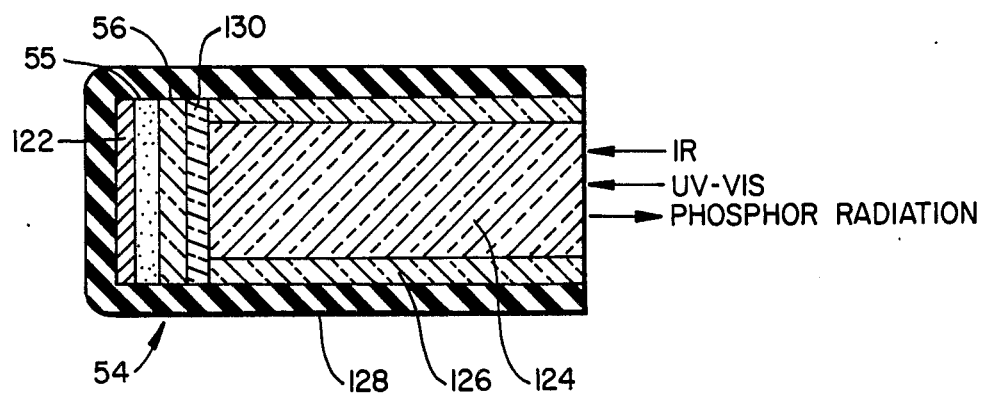
FIG._4A.
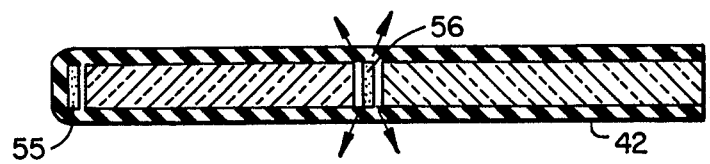
FIG._4B.

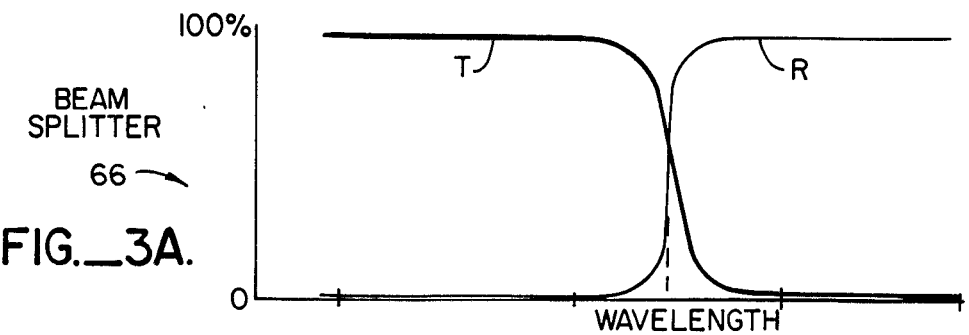
FIG._3A.
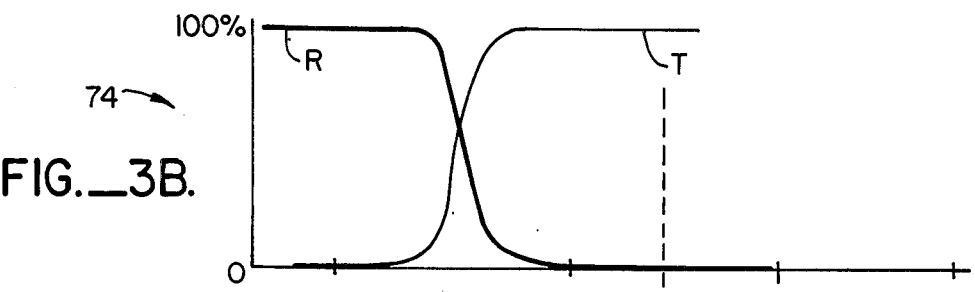
FIG._3B.
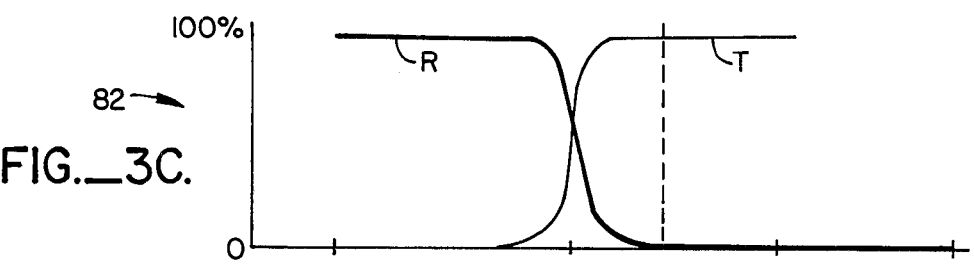
FIG._3C.
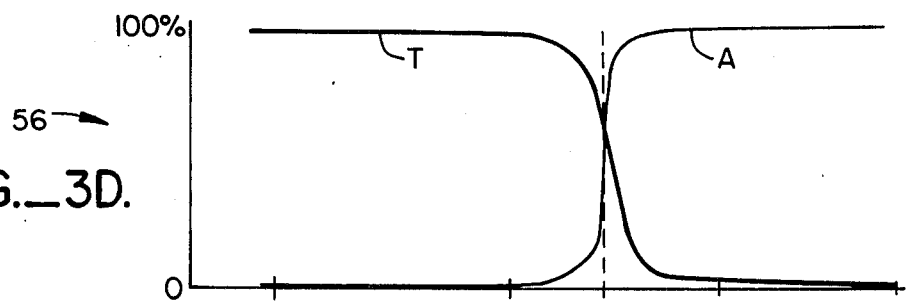
FIG._3D.
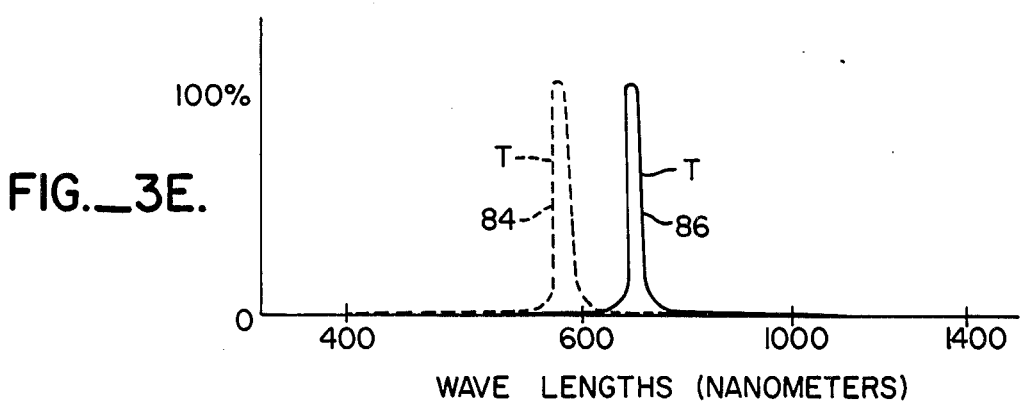
FIG._3E.

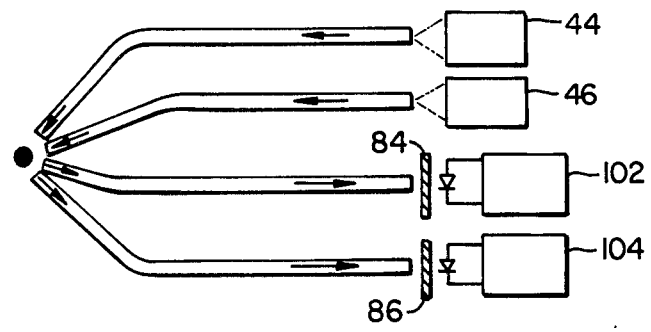
FIG._4C.
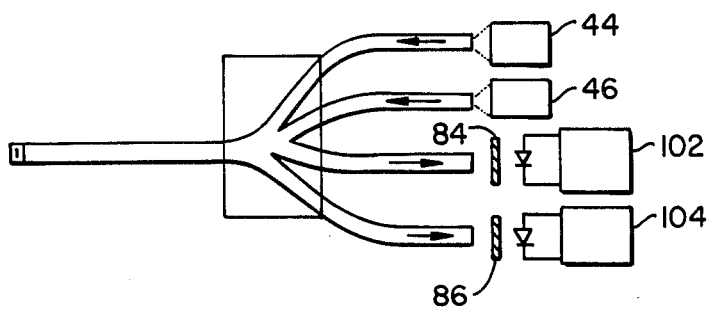
FIG._4D.

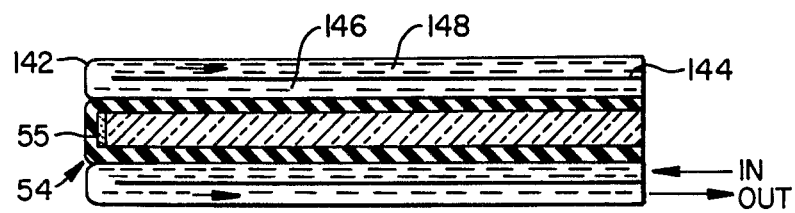
FIG._4E.
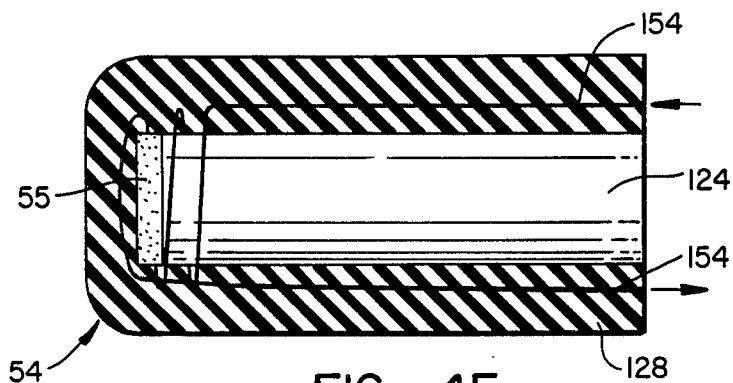
FIG._4F.
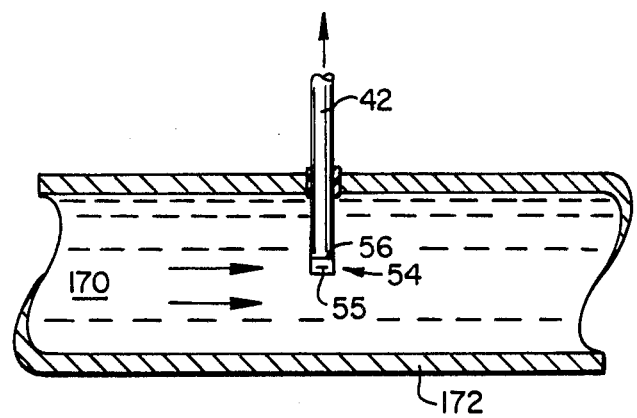
FIG._5A.
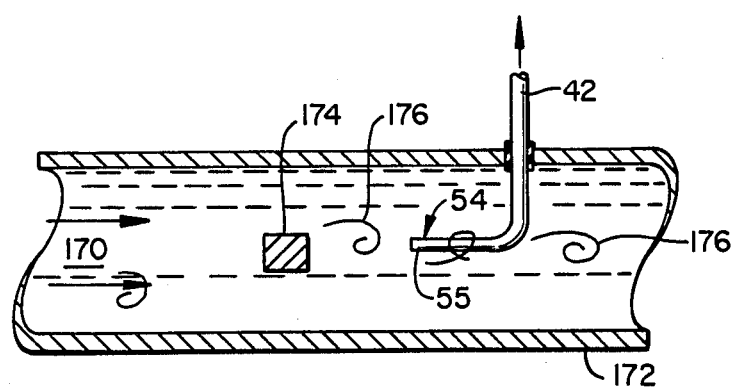
FIG._5B.

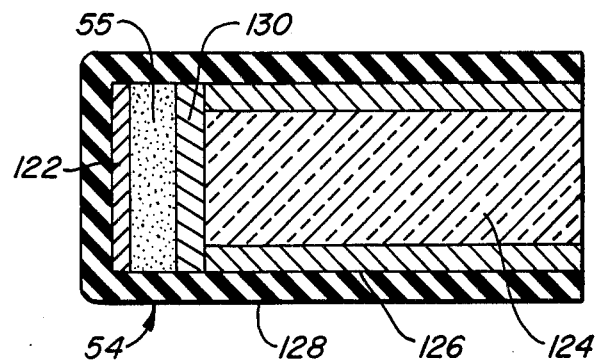
FIG._4G.
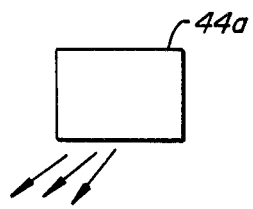
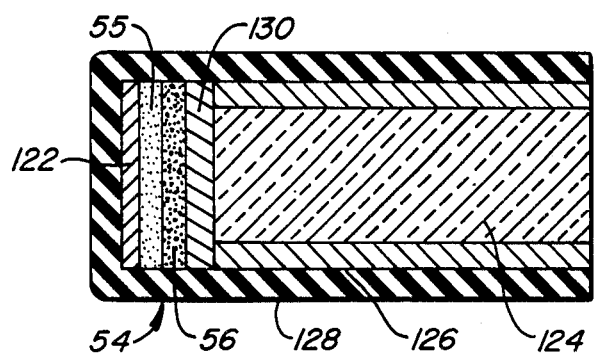
FIG._4H.

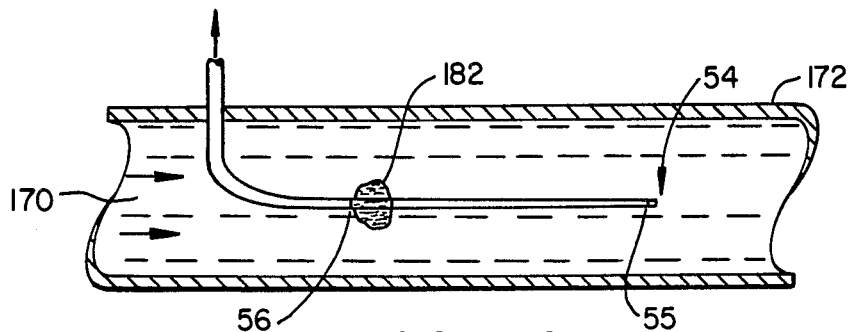
FIG._5C.
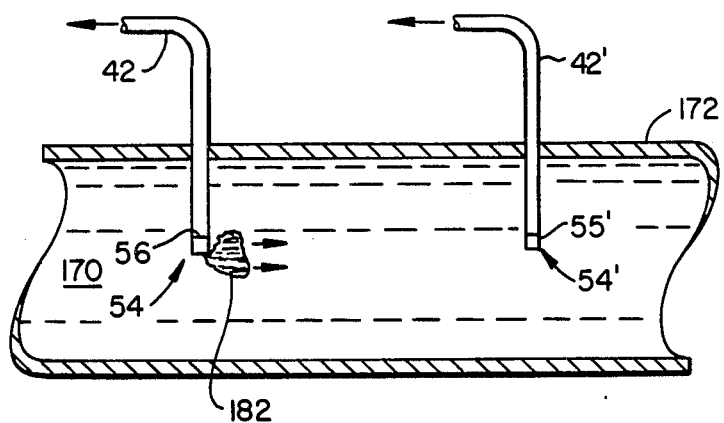
FIG._5D.
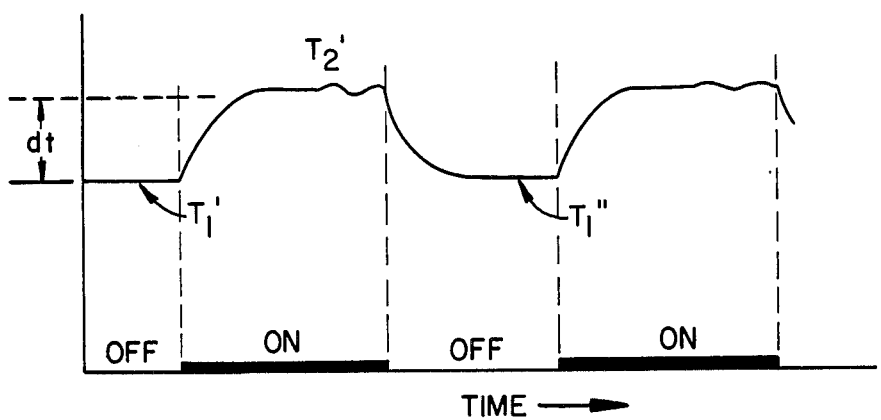
FIG._6.

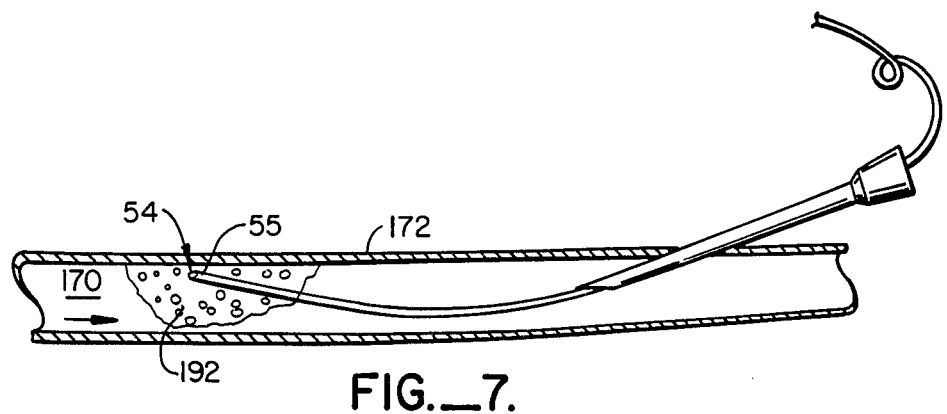
FIG._7.
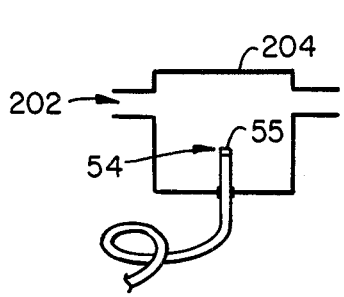
FIG._8.
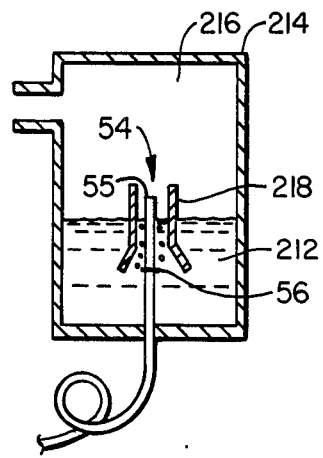
FIG._9.
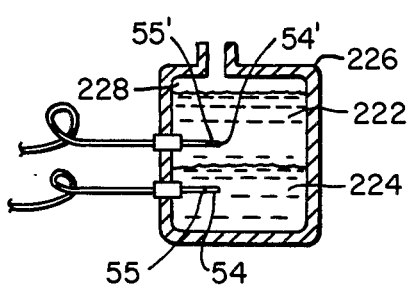
FIG._10A.
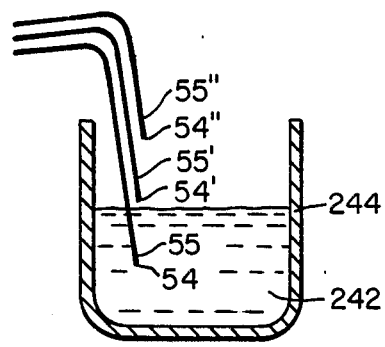
FIG._10B.
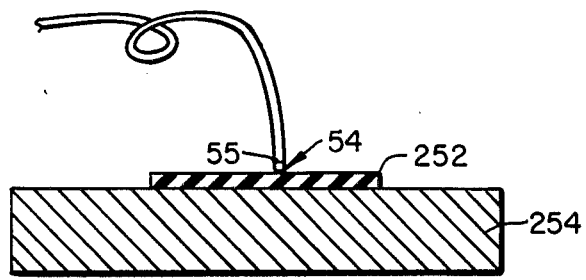
FIG._11.

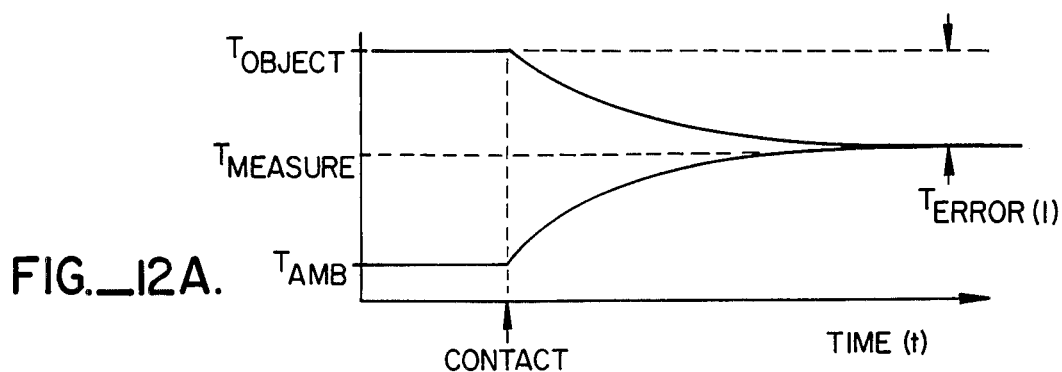
FIG._12A.
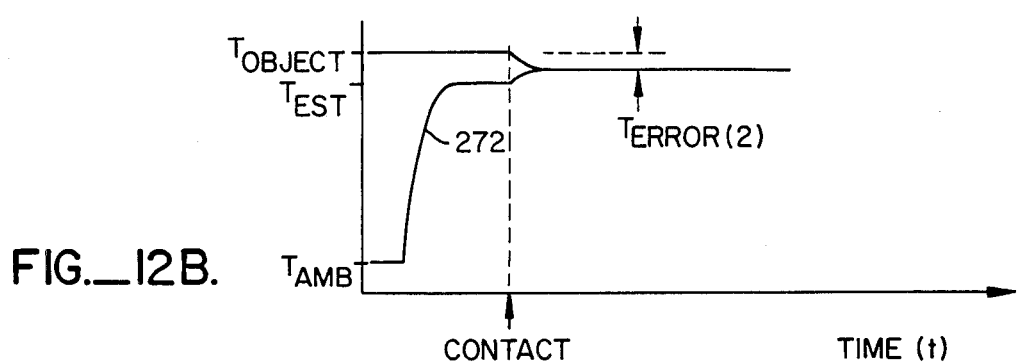
FIG._12B.
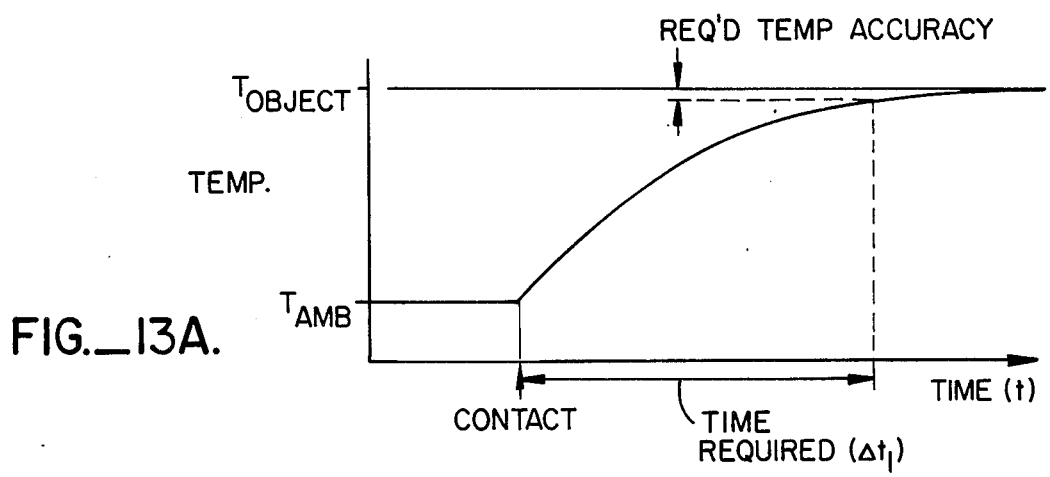
FIG._13A.
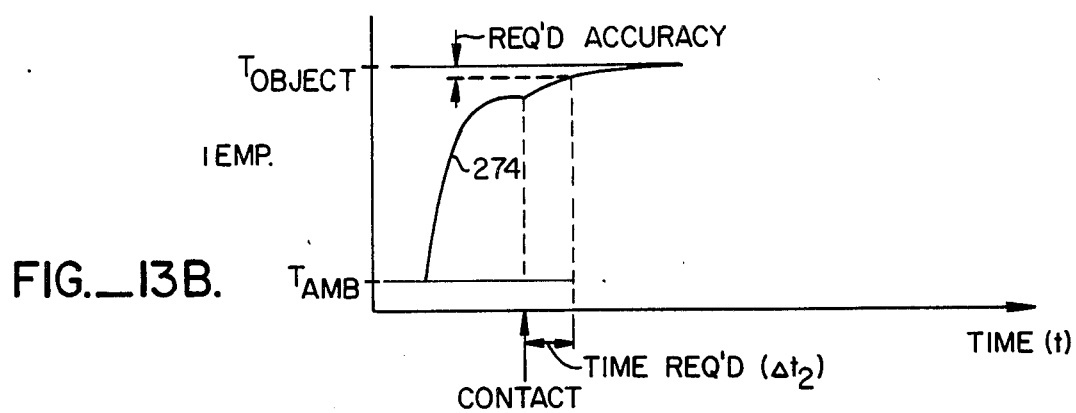
FIG._13B.

4,621,929

FIBER OPTIC THERMAL ANEMOMETER

BACKGROUND OF THE INVENTION

This invention relates in general to testing of materials by their thermal properties and in particular to the testing and measuring of the thermal and physical properties of bodies of solids and fluids by means of fiberoptic techniques.

Physical properties of solids and bodies of fluids have often been measured or tested through measuring or testing their thermal properties. In U.S. Pat. No. 4,344,322 Plapp discloses a device for measuring air flow rate using two hot wire resistors placed in the air intake tube of an internal combustion engine.

In U.S. Pat. No. 4,344,315 Moxon et al. disclosed a device for distinguishing between natural and simulated gems by testing their thermal conductivities. Moxon et al employ a test probe comprising a simple contacting head and a temperature sensing element mounted to a back surface of the head and in thermal contact thereto. The front surface of the contacting head is rounded and adapted to contact gems and has a certain thermal conductivity and hardness. An electrical circuit is connected to the temperature sensing thermistor in the temperature sensing element to provide an indication of temperature change when the heat source thermistor is energized and de-energized. When the round surface of the head is in contact with a gem to be tested, pulses of thermal power are cyclically applied to provide a predetermined amount of heat flow from the probe through the sample gem. The resulting change in temperature of the conducting head is determined by sensing the change in resistance of the sensing thermistor and weighting that change by the sensed thermistor resistance. The change in temperature signal controls a meter and LED which indicate whether the gem is natural or simulated.

The above described devices and methods as well as many other systems used in the prior art are electrical techniques utilizing thermocouples, thermistors or resistance thermometers by means of which electrical signals are generated and then converted into temperature readings or employed for control functions. It is sometimes essential, however, to test or measure the physical properties of materials through their thermal properties by non-electrical techniques. This may occur: (1) where temperatures over large areas are to be measured and measurement by a dense distribution of thermistors or thermocouples thus becomes impractical; (2) where the attachment of thermistors or thermocouples and leads would alter the temperatures to be measured; (3) in environments where because of high electromagnetic fields metallic wires are undesirable; (4) where electrical isolation is described such as in many medical applications; (5) where insensitivity to electrical noise generation is desired; (6) where, because of motion or remoteness of the part to be sensed, permanent lead wires are impractical; or (7) where, because of corrosive chemical environments, wire and thermal couple junctions would be adversely affected, with resultant changes in electrical characteristics. In these situations, optical techniques frequently become preferable. Furthermore, optical fibers may be preferable in many explosive or radioactive environments.

In U.S. Pat. Nos. 4,345,482 Adolfsson et al. disclose a fiberoptic device for measuring physical magnitudes such as force elongation, pressure acceleration and temperature. The device comprises a transducer unit and an electronic unit. The quantity to be measured is supplied to the transducer unit to affect the resonance frequency of an oscillating body included in the transducer unit by changing the dimensions, mass, density, modulus of elasticity and/or mechanical stress of the body. The oscillations of the body are detected optically by means of a fiberoptic position/movement detector. The electronic unit of the fiberoptic device then generates an output signal representative of the oscillations of the body and therefore measures the physical quantity.

SUMMARY OF THE INVENTION

The apparatus of this invention is for testing the thermal heat transfer coefficient of samples. The apparatus comprises a temperature sensitive element having temperature sensitive optical properties and being adapted to contact or be implanted in the sample. The apparatus further comprises means for supplying or withdrawing heat from the element and means for transmitting electromagnetic radiation to the temperature sensitive element. The temperature sensitive optical properties of the element are detected optically by the temperature sensitive element is detected by a detecting means to test the heat transfer coefficient of the sample.

BRIEF DESCRIPTION OF THE DRAWINGS

FIG. 1 is a schematic view of a heat source supplying heat to a body to illustrate an observation upon which the invention is based.

FIG. 2 is a schematic view of an optical and electronic system for supplying heat and measuring temperature to illustrate the preferred embodiment of this invention.

FIGS. 3A, 3B and 3C are graphic illustrations of the reflection, transmission and absorption characteristics of beam splitters of the system in FIG. 2.

FIGS. 3D and 3E are graphical illustrations of the absorption and transmission characteristics of filters in the system of FIG. 2.

FIG. 4A is a cross-sectional view of one end of the fiberoptic portion of the system in FIG. 2 illustrating the preferred embodiment of this invention.

FIG. 4B is a cross-sectional view of an optical fiber illustrating an alternative construction for the optical fiber of FIG. 2.

FIGS. 4C and 4D are schematic views of a fiberoptic system which may be used as alternative constructions for a part of the optical system of FIG. 2.

FIG. 4E is a cross-sectional view of a device for heating or cooling the optical fiber of the system in FIG. 2.

FIG. 4F is a partially cross-sectional and partially elevational view of a section of the optical fiber of FIG. 2 and of a heating coil illustrating an alternative device for heating the fiberoptic in the system of FIG. 2.

FIG. 4G is a cross-sectional view of one end of the fiberoptic portion of the system in FIG. 2 illustrating an alternative construction of the probe tip.

FIG. 4H is a partially cross-sectional and partially schematic view illustrating an alternative system for transferring heat to the temperature sensitive element by radiation.

FIGS. 5A, 5B, 5C and 5D are schematic views illustrating how the optical and electronic system of FIG. 2 may be used to measure the flow rate of a fluid. More specifically, FIG. 5A illustrates a "hot probe" type fiberoptic flow meter. FIG. 5B illustrates a Karman vortex type flow meter. FIG. 5C illustrates a thermal dilution thermal optic flow meter. FIG. 5D illustrates a thermal dilution fiberoptic flow meter utilizing two fiberoptic probes.

FIG. 6 is a graphical illustration of temperature measurement using one fiberoptic probe where the ambient temperature changes during the measurement.

FIG. 7 is a cross-sectional view illustrating how the system of FIG. 2 may be used to detect the presence of air embolism in the blood stream.

FIG. 8 is a schemative view illustrating how the system of FIG. 2 may be used to determine the composition of a mixture of two or more fluids or the pressure of the fluid.

FIG. 9 is a schematic view illustrating how the system of FIG. 2 may be used to determine the pressure of a gas by measuring the boiling point of the liquid under the gas.

FIGS. 10A, 10B are schematic views illustrating how the system of FIG. 2 may be used to determine the levels of fluids.

FIG. 11 is a schematic view illustrating how the system of FIG. 2 may be used to determine the thermal conductivity of a sample.

FIGS. 12A and 12B are graphical illustrations of temperature measurements to illustrate the advantages of preheating or precooling of the fiberoptic probe tip in FIG. 2.

FIGS. 13A, 13B are graphical illustrations of temperature measurements to demonstrate the advantages of preheating or precooling the fiberoptic probe tip of FIG. 2.

DESCRIPTION OF THE PREFERRED EMBODIMENT

According to conventional heat transmission theory, the heat conduction law for solids is $$dq = -kdA(dt/dx)$$

which states that the steady state dq of the rate of heat conduction is proportional to the cross-sectional area dA normal to the direction of flow, and to the temperature gradient, $-dt/dx$, along the conduction path. The quantity k in this expression is known as the thermal conductivity of the material of the solid.

Heat transmission from a solid to a fluid occurs first through a film of the fluid on the surface of the solid. Then the heat transmitted through such film is transmitted to the remainder of the fluid body by convection or movement of the fluid particles themselves. According to conventional heat transmission theory, the law for heat transmission from a solid to a fluid is $$dq = hdAdt$$

which states that in the steady state, dq or the rate of heat transmission is proportional to the cross-sectional area dA normal to the direction of flow and to the temperature difference dt along the transmission path. The quantity h in this expression is called the film coefficient or unit conductance. For a more detailed account on heat transmission theory, see pp. 4-90 to 4-100 of Mark's Standard Handbook for Mechanical Engineers 7th edit., McGraw-Hill, N.Y., 1967.

From the above it will be noted that for heat transmission in both solids and fluids the rate of heat transfer is proportional to the temperature difference dt. For any given solid or body of fluid, a quantity U may be defined as the proportionality constant relating the quantity of heat conducted or convected and the temperature difference. Thus, for heat transmission in both solids and fluids $$dq = Udt$$

where U for the purpose of this application may be called the heat transfer coefficient for the particular solid or body of fluid.

FIG. 1 is a schematic view of a heat source 20 supplying heat to a body 22. Body 22 may be a solid or a body of fluid confined by container. The temperature of surface 24 of body 22 in contact with the heat source is at temperature T1 whereas the temperature of surface 26 opposite the surface 24 is at temperature T2. Then the rate of heat transfer from heat source 20 to body 22 is $$Q = U(T1 - T2)$$

where U is the heat transfer coefficient of body 22. To test or measure the heat transfer coefficient of a solid or body of fluid it is necessary to supply heat to the solid or fluid and to measure the temperatures of the solid or fluid at the point of heat transfer and at a point on a surface opposite to the point of heat transfer.

The heat transfer coefficient of a solid or body of fluid depends on the physical characteristics of the solid or fluid. For fluids or mixtures of fluids, the heat transfer coefficient may indicate the type of fluids, the composition of the mixture of fluids, the flow rate and the pressure of the fluids. By testing the heat transfer coefficient of the fluids or solids, such physical phenomenon can be tested indirectly.

FIG. 2 is a schematic view of an optical and electronic system for supplying heat and measuring temperature to illustrate the preferred embodiment of this invention. As shown in FIG. 2, the optical and electronic system 40 comprises an optical fiber 42, a heat source 44, an excitation source 46, drivers 48,50 for the heat and excitation sources respectively, and the microprocessor 52 for controlling the drivers. Heat source 44 may be any source for supplying heat to the tip 54 of fiberoptic 42. In the preferred embodiment, heat source 44 is an arc or incandescent lamp, infrared emission diode (IRED) or laser for generating radiation which is absorbed by an absorption layer 56 at or near tip 54 of the optical fiber. The location of the absorption layer and other possible configurations in relation to the optical fiber is discussed below. Instead of being a heat source, source 44 may also be a cold sink such as a black surface for absorbing radiation emitted from tip 54 so as to cool it. The transmission of infrared or other radiation between source 44 and tip 54 is accomplished through two lenses 62,64 and beam splitter 66. Beam splitter 66 is such that it reflects the radiation that is transmitted between source 44 and tip 54. Thus, tip 54 of the optical fiber may be heated or cooled and may be used for measuring or testing the heat transfer coefficients of solids and stationary or moving fluids. To cool tip 54, the above-described black surface is cooled by a conventional means. The beam splitter 66 reflects infrared light and light with longer wavelength from tip 54 but transmits light with shorter wavelength and will cause tip 54 to be cooled.

Instead of being an infrared absorption layer, layer 56 may also be an optical filter that absorbs light with frequencies from the infrared through the ultraviolet range. Source 44 may be a laser with its pumping frequency in a narrow band which is absorbed by the filter. Such narrow band may be selected from any number of ranges within the infrared through ultraviolet frequencies provided that the narrow band does not overlap with the frequencies of emission from the luminescent element 55 which emissions are used for determining the temperature of the element or with the frequencies emanating from excitation source 46. Thus, if element 55 is phosphor and the light emission at two distinct frequencies are used for measuring the temperature of the element (as also described below) the narrow band pumping frequency of the laser may be of any frequency separated and apart from those distinct frequencies for phosphor.

From the discussion in reference to FIG. 1 it is clearly desirable to be able to measure the temperature of the solid or fluid at a point of heat transfer. Therefore, it is desirable to be able to measure the temperature of tip 54 conveniently. For such purpose, tip 54 of optical fiber 42 may include therein a luminescent element 55 (shown in FIG. 4A) which emits radiation upon being excited by excitation source 46. In the preferred embodiment, element 55 comprises phosphor, and excitation source transmits ultraviolet or visible light to element 55. Upon being excited, phosphor element 55 will emit radiation whose emission is temperature sensitive. Such emission from element 54 is detected to determine the temperature of the phosphor element. The manner in which the temperature of phosphor may be determined by its radiation is disclosed in U.S. Pat. Nos. 4,075,493 and 4,215,275 to Wickersheim which are incorporated herein by reference. The ultraviolet or visible light from source 46 is transmitted through lens 72, reflected by beam splitter 74 and then transmitted through beam splitter 66 and then focused by lens 62 onto optical fiber 42 to reach element 55. The light emitted by phosphor element 55 is transmitted through optical fiber 42, lens 62, beam splitters 66,74 and then partially reflected and partially transmitted through beam splitter 82, filters 84,86, lenses 88,90 to optical receivers 102,104. Two optical receivers 102,104 are required by the method disclosed in the Wickersheim patent. Beam splitter 66 has the characteristic that it reflects infrared radiation from source 44 or element 55 but transmits the ultraviolet or visible light from source 46 light emitted by element 55. The temperature of element 55 can be determined in accordance with the Wickersheim method. Similarly, beam splitter 74 will reflect ultraviolet or visible radiation from source 46 but transmits light emission from phosphor element 55.

Beam splitter 66 will reflect radiation with wavelengths longer than those of visible and transmit radiation with wavelengths shorter than those of infrared. The spectra of radiation reflected and transmitted by beam splitters 74,82 are similarly broader than those described above. The reflection, transmission and absorption characteristics of beam splitters 66, 74 and 82 are shown in FIGS. 3A, 3B and 3C respectively. The absorption and transmission characteristics of absorbing filter 56 is shown in FIG. 3D, and those of filters 84,86 are shown in FIG. 3E. The transmission characteristics of beam splitter 66 and filter 56 are similar, and their respective reflective and absorption characteristics match.

The temperature of phosphor element 55 may also be determined by exciting the element with light pulses and then measuring the time required (also known as decay time) for the phosphor element to reduce the intensity of its luminescent emission. The decay time is dependent upon the temperature of the phosphor when emission intensity is decreasing, and is an indication of such temperature. Other closely related parameters such as phase are also temperature dependent and may be measured instead of the decay time. Such methods of determining the phosphor temperature is disclosed in U.S. Pat. No. 4,245,507 to Samulski which is incorporated herein by reference. The optical and electronic system of FIG. 2 need only be modified in minor respects for measuring the temperature of the phosphor element 54 by Samulski's method. Thus, source 46 will emit pulses of ultraviolet or visible light. Beam splitter 82, filter 84 and lens 88 and optical receiver 102 may be eliminated. The light received by light receiver 104 is then analyzed with regard to any one of several parameters including intensity, frequency and phase and then used for indicating the temperature of the element 54.

Another fiberoptic temperature sensor that measures the temperature of a sample by the rate of amplitude decay of phosphorescence radiation from phosphor particles is disclosed in U.S. Pat. No. 4,223,226 to Quick et al. After the phosphor particles are stimulated by incident light pulses, the phosphorescent radiation output signals are transmitted to a photodetector and the rate of amplitude decay is measured. The apparatus of FIG. 2 may be modified also in minor respects for measuring the temperature of the phosphor particles by Quick et al.'s method. U.S. Pat. No. 4,223,226 to Quick et al. is incorporated herein by reference.

Also incorporated herein by reference is U.S. Pat. No. 4,374,328 to Tekippe et al. which discloses a photoluminescence indicator. The indicator includes a sample of photoluminescent material having a photoluminescent decay rate which varies as a function of environmental conditions such as temperature or pressure. The sample is optically excited with a modulating signal to generate an excitation output signal functionally dependent on the modulating signal and indicative of the unknown environmental condition. A phase detection means compares the difference in phase between a phase reference signal and the excitation output signal to indicate the photoluminescent decay rate of the sample. Again, with minor adaptations the apparatus of FIG. 2 may be adapted for measuring the temperature of a sample by Tekippe et al.'s method.

Semiconductor temperature sensors are disclosed in U.S. Pat. Nos. 4,136,566 to Christensen and 4,355,910 to Quick et al. which are also incorporated herein by reference. Christensen discloses a temperature sensor utilizing a semiconductor sensing element which absorbs monochromatic radiant energy as a function of temperature. Radiant energy of a specified wavelength at the band edge of a semiconductor is propagated through the semiconductor and is partially absorbed. The radiant energy not absorbed by the semiconductor is detected to indicate the temperature of the semiconductor. With minor modifications, the apparatus of FIG. 2 may be used for measuring temperature by Christensen's method. Thus, the excitation source 46 transmits light of a specified wavelength to a semiconductor element in place of phosphor element 55. Optical receivers 102, 104 are then positioned on the other side of the semiconductor sensor to detect the transmitted light through the sensor. Quick et al. discloses a semiconductor sensor which has optical wavelength-dependent filter characteristics that varies as a function of temperature. The apparatus of FIG. 2 may be modified to measure temperature by Quick et al.'s method in substantially the same manner as for Christensen's method.

Still another alternative device for measuring temperature is the liquid crystal type sensor. Such sensors are disclosed by Rozzell et al. in U.S. Pat. No. 4,016,761 and by Tschirren et al. in U.S. Pat. No. 4,357,106. The apparatus of FIG. 2 is modified so that source 46 will continuously sweep through different wavelengths. The light reflected by the liquid crystal (in place of phosphor element 55) is detected by receivers 102, 104 and analyzed to detect the reflection peaks. The temperature of the liquid crystal can be deduced from the reflection peaks. U.S. Pat. Nos. 4,357,106 and 4,016,761 are incorporated herein by reference.

In U.S. Pat. No. 4,179,927 Saaski discloses an alternative device for measuring temperature. Saaski uses a sensor which includes a gaseous substance that changes in optical density with changes in its temperature. The changes in the properties of light which passes through the gaseous substance represents the temperature of the material. The apparatus of FIG. 2 may be modified in minor respects for measuring temperature using Saaski's sensor.

Yet another device for temperature measuring is U.S. Pat. No. 4,140,393 to Cetas for a birefringent crystal thermometer which uses the temperature dependence of the birefringence of certain single crystals as the temperature sensitive parameter. Polarized light propagates through the crystal in two modes, the ordinary ray and the extraordinary ray which have different indices of refraction. The intensity of light passed through a sandwich of an aligned sheet polarizer, a crystal and an optical analyzer is a function of the birefringence of the crystal. The apparatus of FIG. 2 may be modified in minor respects to practice the method of Cetas. U.S. Pat. No. 4,140,393 is incorporated herein by reference.

In the above description of the preferred embodiment in reference to FIG. 2, optical fiber 42 is used to transmit light between element 54 and sources 44,46 and receivers 102, 104. Such a configuration may allow element 54 to sense the temperature of environments difficult to reach by other means. It will be understood, however, that optical fiber 42 is not essential to the invention. Optical fiber 42 may be eliminated and thus phosphor element 55 and filter 56 placed substantially at the focal point of lens 62. The remaining part of the apparatus of FIG. 2 will function in substantially the same manner as described above for heating element 55 and also for sensing its temperature.

Most of the components of the optical and electronic system 40 of FIG. 2 may be conveniently enclosed within a container 110 shown in dotted lines in FIG. 2. The components of system 40 inside the container particularly the optical components, once set up with the proper distances between one another, will be shielded and protected by the container. End 112 of the optical fiber 42 is connected to the remainder of system 40 by means of connector 114 so that radiation from sources 44,46 are focused onto end 112 for transmission to the phosphor element and the radiation emitted by the phosphor element will be transmitted to receivers 102, 104 as described. Assembled in the above described manner, probe tip 54 of system 40 may be moved conveniently for testing the heat transfer coefficients of samples while the remainder of the system remains stationary and protected. With the above arrangement, it will be simple to dispose of a worn or disfunctional probe by disconnecting optical fiber 42 from container 110. A new and functioning optical fiber with a connector similar to connector 114 may then be connected to the remainder of system 40 inside the container quickly and conveniently.

FIG. 4A is a cross-sectional view of one end of optical fiber 42 illustrating the preferred embodiment of this invention. As shown in FIG. 4A, tip 54 of optical fiber 42 contains a phosphor element 55, absorption filter 56 and an optional reflection layer 122. Optical fiber 42 comprises a fiberoptic core 124 covered by a layer of cladding 126 and protective cover 128. As discussed above, the fiberoptic core 124 transmits infrared and ultraviolet and visible light from the heat and excitation sources towards tip 54. The infrared light or light with other selected frequencies is absorbed by absorption filter 56 and therefore never reaches the phosphor. Such absorption heats up absorption filter 56 which in turns transfers heat to phosphor element 55. Absorption filter 56 transmits the ultraviolet and visible light to phosphor element 55 to excite it. The light emission from the phosphor element is then transmitted through filter 56 and then through the fiberoptic core 124 in the opposite direction. Such emission is then detected and measured to determine the temperature of the phosphor. The optional reflection layer 122 reflects the ultraviolet and visible light not absorbed by phosphor element back into the phosphor element for further absorption and increases the signal to noise ratio of the measurement system. It is possible to replace the phosphor element by one made of liquid crystal, a semiconductor material or birefringent crystal and use the reflection layer 122 to return the transmitted temperature indicating light signal back down the optical fiber 42 to be detected by detectors 102, 104. The protective coating protects the phosphor tip chemically, shields it from extraneous light and mechanically strengthens the optical fiber tip which may serve as a probe.

Where it is desirable to reduce heat transmission between the absorption filter 56 and the fiberoptic core 124, a thermal insulation layer 130 (which is optically clear) may be inserted therebetween. Instead of using a separate heating element as filter 56, the phosphor element can be heated directly by ultraviolet light or other electromagnetic radiation that will be transformed into heat by the phosphor and its chemical binder in the element to heat the phosphor element. Alternatively, a specific heat absorbing medium can be combined with the phosphor and its chemical binder. Such direct heating configurations provide high absorption efficiency. In these configurations, there will be no separate filter element 56 and element 55 may be heated directly and is temperature sensitive as shown in FIG. 4G. Furthermore, the environment surrounding the phosphor element, such as a solid or fluid, may be heated directly. For example a body of black ink or blood may be heated by infrared light.

FIG. 4B is a cross-sectional view of an optical fiber illustrating an alternative construction for the optical fiber 42 of FIG. 2. As shown in FIG. 4B, the heat absorbing filter 56 can be physically separated from the temperature sensing phosphor element 55. This may be desirable where the point of heat radiation needs to be separated from the point of temperature sensing. While only one optical fiber is shown in FIGS. 2, 4A and 4B for the transmission of heating energy and for transmitting energy for exciting the phosphor and for transmitting the light emission from the phosphor element, it will be evident that two, three or four separate optical fibers may be used. If two optical fibers are used, one may be used for transmitting the heat energy to heat the phosphor element through filter 56 and the other optical fiber may be used for transmitting excitation and light emission energy from the phosphor. If three optical fibers are used, then the three kinds of energies may be transmitted each by a different optical fiber. If four optical fibers are used, as shown in FIG. 4C, the light emission from the phosphor is transmitted by two separate fibers for the detection of two different wavelength emissions as taught by Wickersheim. Alternatively, the four optical fibers may merge at their ends near the phosphor element into one fiber as shown in FIG. 4D.

FIG. 4E is a cross-sectional view of a device for heating or cooling the optical fiber 42 to illustrate an alternative device for heating or cooling the phosphor element 55. As shown in FIG. 4E, the entire optical fiber 42, except its very tip, is surrounded by an annular fluid jacket 142. Fluid jacket 142 is divided into two concentric sections by a tube 144: inner section 146 and outer section 148 connected at one end. Fluid of a desirable temperature is supplied to the inner section 146 which then flows around the end of tube 144 into outer section 148. Phosphor element 55 is then heated or cooled to the desired temperature of the fluid. In addition, fiber 42 is protected from external temperature variations. Preferably, tube 144 is a thermal insulator, to reduce heat transmitted between fluids in the two sections.

FIG. 4F is a perspective view of a section of the optical fiber and the heating coil illustrating another alternative device for heating element 55 and the surrounding environment. Current is supplied through leads 154 to heating coil 152 in order to heat the phosphor element 55 to the desired temperature. The two methods described in reference to FIGS. 4E, 4F may be combined with infrared light heating by source 44 and filter 56. All such combinations are within the scope of this invention.

Still other methods and devices for heating phosphor element 55 and the surrounding environment instead of the above described methods are in combination thereof. Such methods and devices include RF electromagnetic, ultrasonic and microwave heating. Employing either the inductive, ultrasonic or microwave heating methods, the probe tip may look essentially similar to tip 54 of FIG. 4A except that layer 56 instead of being an optical filter is a material that absorbs RF electromagnetic, ultrasonic energy energy or microwave energy and converts such energy into heat. Element 56 then transfers heat to the phosphor element to heat it. Such heating systems are shown schematically in FIG. 4H, where RF, ultrasonic or microwave energy is supplied by source 44a to element 56 to heat it.

From the discussion in reference to FIG. 1 for testing or measuring the heat transfer coefficient of a solid or a body of fluid it is necessary usually to measure the temperatures at two different points in the solid or body of fluid. If the heat capacity of the tip is much smaller than that of the sample, and the heating or cooling rate affects only the temperature of a small part of the sample, then frequently measurement of the temperature at only the point of heat transfer will suffice if the temperature of the sample portion away from the tip and unchanged by the heating is known. In reference to FIG. 1, if the heat capacity of body 22 is much greater than that of source 20 and the rate of heat supplied by source 20 is not extraordinarily high, then except for the portion adjacent to source 20, the temperature of the remainder of body 22 remains unchanged. If such temperature T2 is known, then measurement of only T1 will be necessary.

From the discussion in reference to FIG. 1, the heat transmission equation for solids and fluids is $$dq = Udt \quad (1)$$

where U, the heat transfer coefficient, may be used to measure the physical properties of solids and fluids. In one useful application, the rate of heat transmitted, dq, is maintained substantially constant. Then, as the physical properties of the body tested change such as where the body of fluid flows then the temperature difference, dt, will change. Thus, if the temperature differences have been calibrated against different flow rates of a particular fluid then the particular temperature difference indicated by a measuring device, when matched with the calibrated values, will also indicate the flow rate of the particular fluid. The system of FIG. 2, for example, may be so used. In reference to FIG. 2, if the rate of heating or cooling supplied by source 44 is maintained substantially constant and the tip 54 is lowered into the particular fluid and the difference in temperature between phosphor element 55 and the unheated fluid calibrated against the different flow rates of the fluid, then the system of FIG. 2 may be used to measure the flow rate of the same fluid.

In reference again to the equation $dq = Udt$, instead of maintaining dq constant, dt may be maintained substantially constant and the value of U as an indication of changes in physical properties of the body may be calibrated in terms of the rate of heat dq supplied. This will be discussed in more detail below.

Flow Meters

FIGS. 5A, 5B, 5C and 5D are schematic views illustrating how the optical and electronic system of FIG. 2 may be used to measure the flow rate of a fluid. As shown in FIG. 5A, fluid 170 flows through a tube 172. Probe tip 54 of optical fiber 42 is inserted into the tube. Phosphor element 55 is heated or cooled by any one or a combination of the methods described above. The heating of element 55 and/or filter 56 in turn heats up a small portion of the fluid 170 that flows past tip 54. Portion 170 may also be heated by directly shining light on it. The temperature of the fluid that has been heated depends on (1) the temperature of the fluid before heating (2) the heat capacity of the fluid, and (3) the flow rate of fluid 170. Thus, if the flow rate increases, the amount of fluid that has been heated up by tip 54 also increases. Therefore the difference between the temperature of element 55 and the temperature of the unheated fluid would decrease since a greater amount of heat has been carried away per unit time. The decrease in temperature difference thus indicates the amount of increase in the flow rate. Thus, if the amount of heat supplied to heat the fluid is maintained substantially constant, then the variation of the difference in temperature between element 55 and the unheated fluid varies with the flow rate. Hence, the flow rate of the liquid 170 may be calibrated against the difference in temperature of element 55 and the unheated fluid. After the calibration, the temperature reading from element 55 will indicate directly the flow rate if the temperature of the unheated fluid (or fluid upstream of the element) is known.

In equation 1, dt is the difference between the temperature of the phosphor element 55 and the temperature of the fluid before heating. Thus, if the temperature of the fluid is changing, then it is necessary to measure repeatedly both the temperature of the unheated fluid and that of the element. This can be accomplished using two probes or only one probe in the manner described below in reference to FIG. 5D.

How the temperature difference, dt, in equation 1 may be maintained constant by varying the rate of heating or cooling supplied will now be discussed in reference to FIG. 5A and FIG. 2. If the flow rate of fluid 170 increases so that the temperature of the element 55 begins to decrease, such decrease changes the emission spectrum as well as the decay time of light emission by the phosphor element. Such changes are detected by the photoreceivers 102,104 which in turn transmits electrical signals to the microprocessor 52 reflecting the decrease in temperature. Microprocessor 52 processes the signals in accordance with a predetermined computer program and supplies signals to driver 48 to increase the rate of heat supplied to tip 54 by source 44 so as to raise the temperature of phosphor element 55 and to maintain it at a constant temperature. If the temperature of the fluid 170 varies during the measurement in a known manner microprocessor 52 can be programmed in a conventional manner so that the rate of heating supplied to phosphor element 55 will cause its temperature to vary in the same manner in order to maintain a substantially constant dt. It will be evident that the method of maintaining a substantially constant dt may be applied for measuring physical parameters other than flow rates.

If a vortex generating element 174 is placed in the fluid flow 170 as shown in FIG. 5B, vortices 176 will be generated downstream from the generating element 174. It is well known that the frequency of generation of vortices is related to the velocity of the fluid flow. An increase in the velocity of the fluid flow will cause more vortices to be generated. The higher velocity flow associated with the vortices will, as the vortices pass the fiber tip 54, cause momentary drop in the temperature of the probe tip. The frequency of these temperature fluctuations correspond to the frequency of generation of vortices and therefore to the fluid velocity. Thus, the velocity of the fluid flow can be calibrated in terms of the frquency of temperature variations of element 55.

FIG. 5C illustrates how this invention can be used for measuring fluid flow by direct thermal dilution. As shown in FIG. 5C, a bolus 182 of heated fluid (heated by absorption filter 56) moves toward the end of the fiberoptic tip 54 where the change in temperature is detected. The standard way of measuring the time delay and the temperature differences between the heated fluid and non-heated fluid gives the measure of the fluid flow. Instead of using a single fiberoptic as in FIG. 5C, two or more fiberoptics may also be used as illustrated in FIG. 5D. As shown in FIG. 5D, the bolus of liquid 182 is heated by direct absorption of radiation by the fluid or by way of heat transferred from tip 54 which is heated by any one or a combination of methods described above. The bolus flows downstream to tip 54' of optical fiber 42' and its temperature detected. The time delay and temperature difference measurements will indicate the flow rates.

Using two fiberoptic probes to measure flow rates as in FIG. 5D may be advantageous where the unheated or ambient temperature of the fluid changes. Thus, if two probes are used instead of one in measuring the flow rate as in the configuration of FIG. 5A, one probe (which is unheated) can be used to measure the temperature of the unheated fluid and another probe, the one shown in FIG. 5A, used to measure the temperature of the heated fluid. This is particularly advantageous when the unheated or ambient temperature of the fluid changes relatively rapidly. Once the ambient temperature is known as a function of time, the calibration curve for flow rate against temperature assuming a constant rate of heat transfer may be shifted by a time varying amount as determined by the variations in the ambient temperature as detected by one of the probes. Similarly, two probes may also be used in the configuration of FIG. 5B for measuring both the temperature changes caused by the vortices and the temperature of the unheated fluid.

Alternatively, a single fiberoptic probe may be used to perform the same two measurements but at different times by turning the heat source 44 on and off periodically. The temperature detected is shown in the graph of FIG. 6. At a later time the temperatures of the unheated and heated fluids are $T_1''$ and $T_2''$ respectively. If $T_1''$ is different from $T_1''$, then the temperature difference must be computed at different times to measure flow rate accurately. As shown in FIG. 6, at time $T_1'$ the temperature indicated by the system of FIG. 2 is the temperature of the unheated fluid. As the heat source is turned on, the temperature of the phosphor element rises until it reaches a plateau $T_2''$ which indicates the temperature of the heated fluid. The difference between these two temperatures is dt of equation 1. Thus, if the temperature variation of the unheated fluid increases during the measurement, the heat source can be turned on and off periodically at a higher frequency to increase the accuracy of the measurement of dt.

Bubble Detector

In equation 1, U, the heat transfer coefficient also varies with the composition of fluid flow. Thus, if foamy air embolism is present in the bloodstream, its presence changes the heat transfer coefficient since air is much lower in heat conductivity than blood. As shown in FIG. 7, when the air embolism 192 reaches the probe tip 54, the temperature of phosphor element 55 rises. Thus, the presence of air embolism can be detected. The detection of air bubbles in the bloodstream or fluids to be transported to the vascular system is critical since as little as 10 ml of air can, in some individuals, cause sudden vascular collapse and death.

The change in heat transfer coefficient of the bloodstream may be detected using the system of FIG. 2 by either keeping the rate of heating or cooling substantially constant or by maintaining substantially constant the temperature difference between phosphor element 54 and the temperature of the thermally unaffected bloodstream. If the rate of heating or cooling is substantially constant, the arrival of air embolism will cause the temperature of element 55 to change. If the temperature difference is maintained constant, the arrival of air embolism will be indicated by a sudden decrease in the rate of heating or cooling which is required to maintain a substantially constant temperature difference. Since the temperature of the bloodstream usually remains rather constant, the temperature of element 55 will frequently be a direct indication of the presence of air embolism unless there is reason to suspect that the temperature of the bloodstream also fluctuates. Thus, in many medical applications the embolism detector of this invention is capable of detecting the presence of air embolism in a fast and convenient manner.

While only detection of air embolism in bloodstream is discussed in detail herein it will be evident that the same system may be applied to detect the presence of a first fluid in a second fluid if the two fluids are immiscible and have different thermal properties (e.g. conductivities and capacities), such as the presence of gas bubbles in any flowing liquid. All such applications are within the scope of this invention.

Gas Analysis

The heat transfer coefficient also changes for a mixture of two or more gases having different heat capacities and conductivities if their proportions in the mixture change. FIG. 8 illustrates how the apparatus of this invention can be used to detect such change in proportions. The mixture of gas 202 passes through a chamber 204. If the flow rate of gas 202 is relatively slow at the probe tip 54, then the gas flow in chamber 204 does not significantly affect the temperature and heat transfer between tip 54 and gas 202 inside the chamber. If, for instance, the percentage of the gas component having a higher heat conductivity is increased, heat is carried away by gas 202 from phosphor element 55 at a higher rate than previously. Thus, if the temperature of element 55 has been calibrated against different percentages of the components in the mixture of gases then the temperature of the phosphor element will indicate a certain proportion in the mixture.

When the mixture of two or more gasses having different heat capacities and conductivities is analyzed for its composition, the above described technique is sufficient if the ambient or unheated temperature and pressure of the gas mixture stays essentially unchanged during the measurement. If, however, the ambient temperature and pressure of the gas mixture change during such measurement, it will be necessary to measure such ambient temperature and pressure variations with time by using either a second probe spaced apart from the first probe or by turning the one probe used on and off periodically at an appropriate frequency in substantially the same manner as that described above for measuring flow rates. The shape and size and thermal properties of the container defining chamber 204 are not significant provided that chamber 204 defined thereby is large so that at the rate of heating or cooling supplied, the temperature of gas 202 on the whole does not change significantly.

Instead of supplying heat at a constant rate and then measure the gas composition or gas pressure by changes in temperature, the same measurements can alternatively be performed by keeping the temperature substantially constant and measuring the gas composition of pressure by the variations in the rate of heating or cooling supplied. If the ambient temperature and/or pressure change during the measurement, either an additional probe should be used to measure such ambient temperature and pressure or that the same measurement can be made by turning the one probe on and off at an appropriate frequency in substantially the same manner as that for the flow rate measurements discussed above.

Pressure Measurement

FIG. 8 also illustrates how pressure of a gas or other fluid can be measured. If chamber 204 is a vacuum chamber and the gas 202 inside the chamber is being pumped out when element 55 is heated or cooled at a constant rate, then the difference in temperature between element 55 and the unheated gas will rise since there are fewer gas particles to carry away or bring heat to the element. Therefore, if such temperature difference has been calibrated against known pressures of the same gas, then the particular temperature difference will indicate the pressure inside the chamber. If the ambient temperature of the unheated gas changes with time, it will be necessary to measure the ambient temperature repeatedly so that the temperature difference between the element and the unheated gas can be computed. Alternatively, such temperature difference may be kept constant in substantially the same manner as for the flow rate measurement described above, and the pressure of the gas calibrated and measured as a function of the rate of heating or cooling.

Boiling Point Measurement to Indicate Pressure

As shown in FIG. 9, liquid 212 is contained in the container 214. A gas 216 is also in container 214 and above liquid 212. To measure the pressure of gas 216, a tube 218 is placed vertically with one section immersed in the liquid 212. The filter absorber 56 is spaced apart from the phosphor element 55 and is immersed in the liquid within tube 218. Phosphor element 55 remains just above the liquid level to measure the temperature of vapor and thus the boiling point of 212. Heat supplied by filter 56 heats liquid 212 to boiling and the boiling point is indicated by the temperature of element 55. The temperature of phosphor element 55 can be measured by either one of the Wickersheim or Samulski methods discussed above. In contrast to the previous uses of the fiberoptic device, neither the rate of heating nor the temperature difference need to be maintained constant. The heat supplied to the portion of the liquid inside tube 218 should be sufficient to cause it to boil. While use of tube 218 is preferable to reduce the amount of liquid heated to boiling, it will be evident that its use is not essential and may be eliminated if desired. Since the boiling point temperature of liquid 212 is directly related to the pressure in container 214, the temperature at tip 54 provides a measure of this pressure.

Level Indicator

It is often desirable to be able to detect the level of fluid inside a container such as the level of water in a boiler and the presence of water inside a fuel tank. FIGS. 10A, 10B illustrate how the levels of fluids can be detected. A heavier liquid 224 and a lighter liquid 222 are contained in container 226, with a gas 228 above liquid 224 and probe tips 54,54' are located as shown. If the fluid level between liquids 222 and 224 changes so that probe tip 54' becomes immersed in liquid 224 or probe tip 54 becomes immersed in liquid 222, then the temperature of phosphor elements 55,55' would change provided that the two liquids have different heat conductivities. Similarly, if the level of liquid 222 falls below probe tip 54' so that the probe tip is immersed in gas 228, a change in temperature of the phosphor element will also be detected. A mulit-level detector is shown in FIG. 10B. The three probe tips 54, 54' and 54" are arranged at different levels within the container 244. Thus, if container 244 is completely filled with liquid 242, then all three probes will indicate the same heat transfer coefficient. However, as the liquid level falls below probe tip 54", the temperature of the phosphor element 55' will indicate a different heat transfer coefficient. Phosphor element 55' will indicate a similar change in the coefficient as the liquid level falls below probe tip 54'. Such changes will indicate the general location of that fluid level.

Theoretically, more probes will be required if the ambient or the thermally unaffected temperatures of the fluids or liquids vary with time. If, however, the levels between liquids or a gas and a liquid to be detected is between two fluids having widely different heat conductivities, the change in the heat transfer coefficient as the level falls below a probe tip will be much greater than those caused by changes in the ambient temperature. Such is the case in many useful applications such as detecting the level of water in a boiler and the presence of water in gas tank. In such applications, no extra probes will be necessary.

Instead of maintaining constant the rate of heating or cooling as described above substantially the same technique can be applied while maintaining a constant temperature difference between the phosphor elements at probe tips 54, 54' and 54" and the temperatures of the corresponding thermally unaffected fluids in substantially the same manner as that of the flow meter in reference to FIG. 5D above.

Measuring Thermal Conductivity of Solids

Probe tip 54 is shaped to contact the surface of the sample, the thermal conductivity of which is to be determined. The phosphor element 55, being close to the surface of tip 54 in contact with the sample, will have essentially the same temperature as the surface of sample 252 in contact with the probe tip. The sample 252 is placed on a heat sink 254 at a known temperature. If the thickness of the sample 252 at the point of contact with tip 54 and the area of contact between the tip and the sample are known then the thermal conductivity of sample 252 is given by $$dq = -kdAdt/dx$$

where dq is the rate of heat supplied to tip 54, dA is the area of contact between the tip and the sample, dt is the temperature difference between phosphor element 55 and the temperature of heat sink 254 and dx the thickness of sample 252 at the point of contact with the probe tip. The thermal conductivity k can be determined if the other quantities are known or measured.

The apparatus and method of this invention may also be used to differentiate between solids having different heat transfer coefficients even if the solids are not in the shape of sample 252, and are not placed in contact with a heat sink, provided that the solids to be tested are much larger in thermal capacity than tip 54 and that the heat supplied by tip 54 does not significantly change the temperature of most of the solid. Then the geometrical factors and sizes of different solids do not matter and different materials having different conductivities can be differentiated simply by the temperature of phosphor element 55 when tip 54 is in contact with the solids.

It will be noted that in the above measurement of thermal conductivity it is assumed that all the heat supplied to tip 54 is conducted through sample 252 to heat sink 254 and that no significant amount of heat is conducted away to the environment 254. To increase the accuracy of the above measurement, it may be preferable that tip 54 and optical fiber 42 be kept at a controlled temperature such as by means of the heating or cooling fluid jacket 142 illustrated in FIG. 4E.

Applications of the Two Probe and One Probe Techniques to Above Measurements The above-described techniques using one or two probes in reference to FIGS. 5D, 6 for measuring the temperatures of the phosphor element and of the unheated fluid is useful for most of the applications described above. Where the ambient temperature of the unheated fluid changes relatively rapidly, measurement of the ambient temperature of the unheated fluid may be crucial. Thus in measuring the flow rate of a fluid, the composition of a gas mixture, the pressure of a fluid, the physical parameter measured is calibrated against dt, the difference in temperature between the phosphor element and the unheated fluid. Thus, if the temperature of the unheated fluid changes, repeated measurements of such temperature will be required. When the flow rate of a fluid is measured by the frequency of generation of vortices as described above, changes in ambient temperature of the unheated fluid may appear as noise in such frequency measurement. Therefore, measurement of the ambient temperature will reduce such noise. Sudden changes in ambient temperature may also appear as noise in the above-described thermal dilution, level indication and bubble detection techniques. Thus, repeatedly measuring the ambient temperature of the unheated fluid will also help to reduce such noise. If a second probe is employed to measure the ambient temperature of the unheated fluid, such probe will not be used for heating or cooling purposes but only for temperature sensing.

Temperature Conditioning

Where the sample to be tested is small in heat capacity as compared to the probe tip, it may be desirable to heat or cool the probe tip so that its temperature is close to the tempatature of the sample it is heating or measuring. The first advantage of temperature conditioning the probe tip is that for measurements involving small objects such as semiconductor devices, the measurement errors are significantly reduced. For example, assume that the sample has the same heat capacity as the probe tip, that initially the sample is at 100° F. and the probe tip is at 70° F. Then when a steady state is reached after the probe tip contacts the sample, the temperatures of the probe tip and the sample converge to 85°. Thus, the measurement of the temperature of the sample is off by 15° from the correct value 100° F. The temperatures of the sample and of the probe tip are shown in FIG. 12A. If, however, the probe tip has been preheated (curve 272) before contacting the sample as illustrated in FIG. 12B, then upon contact the resulting temperature of both the sample and the probe tip will be very close to that of the true temperature of the sample before contact. Thus, the error in temperature measurement without preheating is $T_{error}(1)$ as illustrated in FIG. 12A. With preheating, however, the error in temperature measurement has been reduced to $T_{error}(2)$.

Another advantage in preheating or precooling the probe tip to a temperature close to that of the sample is that much less time will be required to perform the measurement. Such effect is illustrated in FIGS. 13A and 13B. As shown in FIG. 13A, considerable time delta $T_1$ is required to heat or cool the sample so that the temperature of the sample is substantially the same as that of the probe tip. If the probe tip has been preheated or precooled to a temperature (curve 274) close to that of the sample as illustrated in FIG. 13B, the time required to perform the measurement delta $T_2$ is less than delta $T_1$.

The above descripton of method and construction used is merely illustrative thereof and various changes in shapes and sizes, materials or other details of the method of construction may be within the scope of the appended claims.

What is claimed is:

1. An apparatus for testing the heat transfer coefficient of a sample in an environment comprising:
   an element having temperature sensitive optical properties and being adapted to contact or to be implanted in the sample;
   radiation heat transfer means for directly supplying heat to the element;
   means for transmitting electromagnetic radiation to said element; and
   means for optically detecting said temperature sensitive optical properties of the element to test the heat transfer coefficient of the sample, whereby the difference between the temperature of the element and that of the environment is an indication of the heat transfer coefficient of the sample.

2. The apparatus of claim 1, further comprising a length of optical fiber having a first and a second end, wherein said element is held at the first end of said fiber and wherein said transmitting means and detecting means are held at the second end of the fiber.

3. A probe apparatus for testing the heat transfer coefficient of a sample in an environment, comprising:
   a length of optical fiber having a first and a second end; and
   an element held in optical communication with the first end of said optical fiber, said element having temperature sensitive optical properties and being adapted to contact or to be implanted in the sample, wherein the second end of the optical fiber is adapted to be connected to (a) a radiation heat transfer means for directly heating the element, (b) means for transmitting electromagnetic radiation to said element and (c) means for detecting the temperature of the element optically, in order to test the heat transfer coefficient of the sample whereby the difference between the temperature of the element and that of the environment is an indication of the heat transfer coefficient.

4. The apparatus of claims 1 or 3, wherein the radiation heat transfer means supplies heat at a substantially constant rate from said sample so that the heat transfer coefficient of the sample is inversely related to the difference between the temperature of the element and the ambient temperature.

5. The apparatus of claim 3, wherein the heat capacity of the sample is much greater than that of the element and the rate of heating of the sample is such that the ambient temperature of a large portion of the sample is substantially unaltered thereby.

6. The apparatus of claims 1 or 3, wherein the radiation heat transfer means supplies heat at such rate that the difference between the temperature of the element in contact with the sample and the ambient temperature is substantially constant, so that the heat transfer coefficient of the sample is proportional to the rate of heating.

7. The apparatus of claim 6, wherein the heat capacity of the sample is much greater than that of the element and the rate of heating of the sample is such that the ambient temperature of the sample is substantially unaltered thereby so that when such ambient temperature remains substantially constant, the temperature of the element is maintained substantially constant.

8. The apparatus of claims 1 or 3 wherein the temperature sensitive element includes a luminescent material in its composition.

9. The apparatus of claim 8, further comprising means for detecting the intensities of radiation at two distinct wavelengths from the luminescent material in said element to determine the temperature of the temperature sensitive element.

10. The apparatus of claim 8, further comprising means for detecting the luminescent response of the luminescent material in said element over time to determine the temperature of the temperature sensitive element.

11. The apparatus of claim 10, wherein said luminescent response detecting means detects a parameter indicative of the luminescent decay time of the luminescent material.

12. The apparatus of claims 1 or 3 wherein the temperature sensitive element is a liquid crystal sensor whose light reflectance is a function of its temperature.

13. The apparatus of claims 1 or 3 wherein the temperature sensitive element includes a semiconductor material which absorbs light energy as a function of temperature.

14. The apparatus of claims 1 or 3 wherein the temperature sensitive element includes a luminescent material and wherein said radiation heat transfer means comprises:
   an optical filter that absorbs electromagnetic radiation, said filter placed in heat conductive relationship with the element; and
   source for supplying electromagnetic radiation to said filter for heating the elements by heating the optical filter.

15. The apparatus of claim 14 wherein the optical filter absorbs electromagnetic radiation in a manner that does not interfere substantially with the transmission of electromagnetic radiation by the transmitting means to said element.

16. The apparatus of claim 14 wherein the optical filter and the temperature sensitive element is one member comprising a heat absorbing medium into which a temperature sensitive material is dispersed.

17. The apparatus of claim 16 wherein the temperature sensitive material is phosphor.

18. The apparatus of claims 2 or 3 wherein the temperature sensitive element includes a luminescent material and wherein said radiation heat transfer means comprises:
   an optical filter that absorbs light in a manner which does not interfere substantially with the transmission of electromagnetic radiation to said element by the transmitting means and with the optical detection of the temperature of the element, said filter placed between said first end and the element and in heat conductive relationship with the element; and
   source for supplying light to said second end, said light being transmitted by the optical fiber to its first end for heating the element by heating the optical filter.

19. The apparatus of claim 18 wherein the optical filter absorbs light within a frequency range which does not overlap with the frequencies of radiation emitted by the element and of radiation transmitted by the transmitting means.

20. The apparatus of claim 19 wherein the optical filter absorbs infrared light.

21. The apparatus of claims 2 or 3 wherein the temperature sensitive element includes phosphor in its composition and wherein said radiation heat transfer means comprises a source for supplying ultraviolet light to said second end which is then transmitted by the optical fiber to the phosphor in the temperature sensitive element to heat the element.

22. The apparatus of claims 1 or 3 wherein said radiation heat transfer means comprises:
a heating member which absorbs radio frequency electromagnetic waves, said heating member being placed in heat conductive relationship with said element; and
means for supplying radio frequency electromagnetic waves to said heating member to supply heat to said element.

23. The apparatus of claims 1 or 3 wherein said radiation heat transfer means comprises:
a heating member which absorbs ultrasonic waves, said heating member being placed in heat conductive relationship with said element; and
a source for supplying ultrasonic waves to said heating member.

24. The apparatus of claims 1 or 3 wherein said radiation heat transfer means comprises means for supplying heat to a medium surrounding the element.

25. A probe apparatus for testing the heat transfer coefficient of a sample in an environment, comprising:
a length of optical fiber;
an element held in optical communication with a first end of said optical fiber, said element having temperature sensitive optical properties and being adapted to contact or to be implanted in the sample; and
radiation heat transfer means for directly supplying heat to the element to test the heat transfer coefficient of the sample whereby the difference between the temperature of the element and that of the environment is an indication of the heat transfer coefficient of the sample.

26. An apparatus for testing the heat transfer coefficient of a sample in an environment comprising:
a length of optical fiber;
an element held in optical communication with one end of said fiber, said element having temperature sensitive optical properties and being adapted to contact or to be implanted in the sample;
radiation heat transfer means for directly supplying heat to the element;
means at the other end of the fiber for transmitting electromagnetic radiation to said element; and
means at the other end of the fiber for optically detecting said temperature sensitive optical properties of the element to test the heat transfer coefficient of the sample whereby the difference between the temperature of the element and that of the environment is an indication of the heat transfer coefficient of the sample.

27. An apparatus for testing the thermal heat transfer coefficient of a sample in an environment comprising:
a first length of optical fiber;
a temperature sensitive element held at a first end of said optical fiber, said element having temperature sensitive luminescent properties and being adapted to contact or to be implanted in the sample;
radiation heat transfer means for directly supplying heat to the element;
means at the second end of the optical fiber for exciting said temperature sensitive element; and
means at said second end of the optical fiber for optically detecting the temperature sensitive luminescent properties of said element to test the heat transfer coefficient of the sample whereby the difference between the temperature of the element and that of the environment is an indication of the heat transfer coefficient of the sample.

28. The apparatus of claim 27 wherein said element includes phosphor in its composition and wherein said means for exciting said temperature sensitive element comprises a source of ultraviolet light.

29. The apparatus of claim 28, wherein said radiation heat transfer means comprises an infrared light source, said apparatus further comprising four additional optical fibers in optical communication with said first length of optical fiber, the four additional lengths of optical fibers being so spatially oriented that a first additional optic fiber is used to transmit ultraviolet light from the exciting means to said element, a second additional optical fiber transmits infrared light from the infrared light source to said element, a third and a fourth additional optical fiber for transmitting the electromagnetic transmission from said element to detectors for detecting the intensities of radiation at two distinct wavelengths from the phosphor in said element.

30. An apparatus for measuring the flow rate of a fluid comprising:
a length of optical fiber;
a temperature sensitive element held at a first end of said optical fiber, said element having temperature sensitive luminescent properties and being adapted to be placed in the flowing fluid;
radiation heat transfer means for directly supplying heat to the element;
means at the second end of the optical fiber for exciting said temperature sensitive element; and
means at the second end of the optical fiber for detecting electromagnetic radiation emitted by said element to indicate the flow rate of the fluid whereby the difference between the temperature of the element and that of the unheated fluid is an indication of the flow rate.

31. The apparatus of claim 30 wherein the radiation heat transfer means supplies heat to the element at a substantially constant rate so that the flow rate of the fluid varies inversely with the difference in temperature between the element and the fluid thermally unaffected by the radiation heat transfer means.

32. The apparatus of claim 30 wherein the radiation heat transfer means supplies heat at such a rate that the difference in temperature between the element and the fluid thermally unaffected by the radiation heat transfer means remains substantially constant so that the flow rate of the fluid varies directly with the rate of heating of the element.

33. A method for measuring the flow rate of a fluid by means of an element having temperature sensitive luminescent properties, said method comprising:
- placing the temperature sensitive element in the flowing fluid;
- directly supplying heat to the element;
- exciting said temperature sensitive element to luminescence;
- detecting the electromagnetic radiation emitted by said element to detect the temperature of the element; and
- detecting the temperature of the unheated fluid so that the difference between the temperature of the element and that of the unheated fluid is an indication of the flow rate of the fluid.

34. An apparatus for measuring the flow rate of a fluid comprising:
- a length of optical fiber;
- a temperature sensitive element held at one end of said fiber optic, said element having temperature sensitive luminescent properties and being adapted to be placed in the flowing fluid;
- a vortex generating element also placed in the flowing fluid but at a location upstream relative to said element so that vortices generated thereby will come into contact with the element;
- radiation heat transfer means for directly supplying heat to the element;
- means at a second end of the optical fiber for exciting said temperature sensitive element; and
- means at a second end of the optical fiber for detecting electromagnetic radiation emitted by said element to determine the frequency of generation of vortices which indicates the flow rate of the fluid.

35. The apparatus of claim 34 wherein the radiation heat transfer means supplies heat to the element at a substantially constant rate so that when the vortex comes into contact with the first end of said fiber, the higher flow rate of the vortex will cause the temperature of said element to fluctuate so that the frequency of such temperature fluctuations will indicate the frequency of generation of the vortices.

36. The apparatus of claim 34 wherein the radiation heat transfer means supplies heat at such a rate that the difference in temperature between the element and the fluid thermally unaffected by the radiation heat transfer means remains substantially constant so that when a vortex reaches the first end of said fiber, the high flow rate of the fluid at the vortic will cause the rate of heat supplied to the element to increase momentarily so that the frequency of such momentary increases in the heat transfer rate will indicate the frequency of generation of the vortices.

37. A method for measuring the flow rate of a fluid by means of an element having temperature sensitive luminescent properties and a vortex generating element, said method comprising:
- placing the temperature sensitive element in the flowing fluid;
- placing the vortex generating element in the flowing fluid at a location upstream relative to said element so that vortices generated thereby will come into contact with the element;
- directly supplying heat to the element;
- exciting said temperature sensitive element to luminescence; and
- detecting the electromagnetic radiation emitted by said element to determine the frequency of generation of vortices which indicates the flow rate of the fluid.

38. An apparatus for measuring the flow rate of a fluid comprising:
- a length of optical fiber;
- a temperature sensitive element held at one end of said fiber, said element having temperature sensitive luminescent properties and being adapted to be placed in the flowing fluid;
- radiation heat transfer means for supplying heat to a bolus of fluid at a known distance upstream from said element;
- means at a second end of the optical fiber for exciting said temperature sensitive element; and
- means at said second end of the optical fiber for detecting electromagnetic radiation emitted by said element to determine the time of arrival and temperature differences of said bolus of fluid at the element thereby also determining the flow rate of the fluid wherein the radiation heat transfer means comprises means for heating a portion of the optical fiber between the first and second ends, said portion being placed upstream and at a known distance from said element.

39. The apparatus of claim 38 wherein said means for heating a portion of the optical fiber comprises:
- an optical filter that absorbs electromagnetic radiation but transmits at least some light emitted by said element upon excitation, said filter placed between said first and second ends of the optical fiber; and
- source for supplying electromagnetic radiation to said second end of the fiber for heating the optical filter.

40. An apparatus for measuring the flow rate of a fluid comprising:
- a length of optical fiber;
- a temperature sensitive element held at one end or said fiber, said element having temperature sensitive luminescent properties and being adapted to be placed in the flowing fluid;
- a radiation heat transfer means for supplying heat to a bolus of fluid at a known distance upstream from said element;
- means at a second end of the optical fiber for exciting said temperature sensitive element and;
- means at said second end of the optical fiber for detecting electromagnetic radiation emitted by said element to determine the time of arrival and temperature differences of said bolus of fluid at the element thereby also determining the flow rate of the fluid, wherein said radiation transfer means comprises:
  - a length of a second optical fiber adapted to be placed in the fluid upstream from said element;
  - an optical filter that absorbs electromagnetic radiation, said filter being implanted in said second optic fiber so that heating of the filter will cause heat to be transferred between the filter and the fluid surrounding the second optical fiber; and
  - source for supplying a pulse of electromagnetic radiation to said second optical fiber for heating the filter momentarily so that the bolus of fluid surrounding the filter will be heated before it reaches said element.

41. A method for measuring the flow rate of a fluid by means of a length of optical fiber and an element having temperature sensitive luminescent properties placed at one end of the optical fiber, said method comprising:

placing the temperature sensitive element and said one end of the optical fiber in the flowing fluid;

directly supplying heat to a portion of the optical fiber for heating a bolus of fluid at a known distance upstream from said element;

exciting said temperature sensitive element to luminescence; and detecting the electromagnetic radiation emitted by said element to determine the time of travel and temperature differences of said bolus of fluid thereby also determining the flow rate of the fluid.

42. An apparatus for detecting the presence of a first fluid in a second fluid, said two fluids being immiscible and having different thermal properties, said apparatus comprising:

a length of optical fiber a first end of which is adapted to be inserted into the second fluid;

a temperature sensitive element held at the first end of said fiber, said element having temperature sensitive luminescent properties;

radiation heat transfer means for directly supplying heat to the element;

means at a second end of the optical fiber for exciting said temperature sensitive element; and means at a second end of the optical fiber for detecting electromagnetic radiation emitted by said element to detect the temperature of the element and the presence of the first fluid whereby such presence is indicated by a change in temperature of the element.

43. The apparatus of claim 42 wherein the radiation heat transfer means supplies heat to the element at a substantially constant rate so that the presence of the first fluid is indicated by a change in temperature of said element.

44. The apparatus of claim 42 wherein the radiation heat transfer means supplies heat to the element at such rate that the difference in temperature between the element and the second fluid thermally unaffected by the radiation heat transfer means remains substantially constant so that the presence of the first fluid is indicated by a change in the rate of heat supplied or withdrawn from the element.

45. The apparatus of claim 42 wherein said first fluid is a gas and said second fluid is a liquid.

46. The apparatus of claim 45 wherein the liquid is blood and the gas to be detected is air embolism.

47. A method for detecting the presence of a first fluid in a second fluid said two fluids being immiscible and having different thermal properties by means of an element having temperature sensitive luminescent properties, said method comprising:

placing the temperature sensitive element in the second fluid;

directly supplying heat to the element;

exciting said temperature sensitive element to luminescence; and detecting the electromagnetic radiation emitted by said element to detect the temperature of the element and the presence of the first fluid in the second fluid whereby such presence is indicated by a change in temperature of the element.

48. An apparatus for determining the composition of a mixture of fluids having different heat capacities and conductivities, comprising:

a length of optical fiber;

a temperature sensitive element held at a first end of said optical fiber, said element having temperature sensitive luminescent properties and being adapted to be placed in the fluid mixture;

radiation heat transfer means for directly supplying heat to the element;

means at a second end of the optical fiber for exciting said temperature sensitive element; and means at a second end of the optical fiber for detecting electromagnetic radiation emitted by said element to indicate the temperature of the element and the composition of the fluid mixture whereby the temperature of the element is an indication of the composition of the fluid mixture.

49. The apparatus of claim 48 wherein the radiation heat transfer means supplies heat to the element at a substantially constant rate so that the proportion of a fluid in the fluid mixture with a lower thermal capacity and conductivity varies inversely with a difference in temperature between the element and the fluid mixture thermally unaffected by the radiation heat transfer means.

50. The apparatus of claim 48 wherein the radiation heat transfer means supplies heat at such a rate that the difference in temperature between the element and the fluid mixture thermally unaffected by the heat transfer means remains substantially constant so that the proportion of the fluid in the mixture with a smaller heat capacity and heat conductance varies directly with the rate of heating of the element.

51. An apparatus for measuring the pressure of a fluid comprising:

a length of optical fiber;

a temperature sensitive element held at a first end of said optical fiber, said element having temperature sensitive luminescent properties and being adapted to be placed in the fluid;

radiation heat transfer means for directly supplying heat to the element;

means at the second end of the optical fiber for exciting said temperature sensitive element; and means at the second end of the optical fiber for detecting electromagnetic radiation emitted by said element to detect the temperature of the element and the pressure of the fluid whereby the temperature of the element is an indication of the pressure of the fluid.

52. The apparatus of claim 51 wherein the radiation heat transfer means supplies heat to the element at a substantially constant rate so that the pressure of the fluid varies inversely with a difference in temperature between the elements and the fluid thermally unaffected by the radiation heat transfer means.

53. The apparatus of claim 51 wherein the radiation heat transfer means supplies heat at such a rate that the difference in temperature between the element and the fluid thermally unaffected by the radiation heat transfer means remains substantially constant so that the pressure of the fluid varies directly with the rate of heating or cooling of the element.

54. A method for measuring the pressure of a fluid by means of an element having temperature sensitive luminescent properties, said method comprising:

placing the temperature sensitive element in the fluid;

directly supplying heat to the element;

exciting said temperature sensitive element to luminescence; and detecting the electromagnetic radiation emitted by said element to detect the temperature of the element, said temperature being an indication of the pressure of the fluid.

55. An apparatus for measuring the pressure of a gas above a liquid comprising:
   a length of optical fiber;
   a temperature sensitive element held at a first end of said optical fiber, said element having temperature sensitive luminescent properties and being adapted to be placed in the gas at a location immediately above the surface of the liquid;
   means for heating the liquid to boiling state;
   means at the second end of the optical fiber for exciting said temperature sensitive element; and
   means at a second end of the optical fiber for detecting electromagnetic radiation emitted by said element to determine the temperature of the vapor from the boiling liquid said temperature being an indication of the pressure of the gas.

56. A method for measuring the pressure of a gas above a liquid by means of an element having temperature sensitive luminescent properties, said method comprising:
   placing the temperature sensitive element in the gas at a location immediately above the surface of the liquid;
   heating the liquid to a boiling state;
   exciting said temperature sensitive element to luminescence; and
   detecting the electromagnetic radiation emitted by said element to determine the temperature of the vapor from the boiling liquid said temperature being an indication of the pressure of the gas.

57. An apparatus for determining levels between immiscible fluids having different thermal capacities and conductivities, said apparatus comprising:
   a plurality of optical fibers, each fiber being placed with its first end placed at a desired location in one of the fluids for determining the level between said fluid and the fluid immediately above;
   a temperature sensitive element held at each of the first ends of said plurality of optical fibers, said element having temperature sensitive luminescent properties and being adapted to be placed in the corresponding fluid;
   radiation heat transfer means for directly supplying heat to each of the elements;
   means at the second end of each optical fiber for exciting the temperature sensitive element held at the first end of such fiber; and
   means at the second end of each optical fiber for detecting electromagnetic radiation emitted by the element held to such fiber to detect the temperature of each element, said temperature being an indication of the levels between the fluids.

58. The apparatus of claim 57 wherein the radiation heat transfer means supplies heat to each element at a substantially constant rate so that when the level between the fluid in which the element is placed and the fluid immediately above falls below the level of said element, such change in level is indicated by a change in temperature of such element.

59. The apparatus of claims 31, 35, 43, 49, 52 or 58 further comprising means for measuring the temperature of the thermally unaffected fluid.

60. The apparatus of claim 59 wherein said temperature measuring means comprises:
   a length of a second optical fiber;
   a second element held at one end of said second optical fiber, said second element having temperature sensitive luminescent properties and being adapted to be placed in the fluid at a location substantially unaffected by the heating by the radiation heat transfer means;
   means at the other end of the optical fiber for exciting said second element; and
   means at said other end of the fiber for detecting the electromagnetic radiation emitted by said second element to determine the temperature of the thermally unaffected fluid.

61. The apparatus of claims 31, 35, 43, 49, 52 or 58 further comprising means for turning the radiation heat transfer means on and off periodically, so that the radiation detected by the detecting means at a time during which the radiation heat transfer means is on indicates the temperature of the element when it is heated, and the radiation detected at a selected time after the radiation heat transfer means is turned off indicates the temperature of the thermally unaffected fluid at such time.

62. The apparatus of claim 61 wherein said means for turning on and off the radiation heat transfer means is adapted to turn on and off the radiation heat transfer means at a selected rate that corresponds to the rapidity of temperature variations of the fluid thermally unaffected by the radiation heat transfer means.

63. The apparatus of claim 57 wherein the radiation heat transfer means supplies heat to each element at such rate that the difference in temperature between such element and the portion of the fluid thermally unaffected by the radiation heat transfer means remains substantially constant so that when the level between the fluid into which such element is placed and the fluid immediately above falls below the level of such element such change in level is indicated by a rise in the rate of heat supplied to the element.

64. The apparatus of claims 32, 36, 44, 50 or 63 wherein the radiation heat transfer means includes a control means comprising:
   means for measuring the temperature of the thermally unaffected fluid; and
   means responsive to the difference between the temperature of the element and that of the thermally unaffected fluid for changing, when required, the rate of heating so that such difference remains substantially constant.

65. A method for determining the level between two immiscible fluids having different thermal properties as the level changes, with an element having temperature sensitive luminescent properties, said method comprising:
   placing the temperature sensitive element at a desired location in the fluid with the lower altitude for determining the level between said fluid and the fluid above;
   directly supplying heat to the element;
   exciting the temperature sensitive element to luminescence; and
   detecting the electromagnetic radiation emitted by the element to detect the temperature of the element, said temperature being an indication of the level between the fluids as it changes.

66. An apparatus for measuring the thermal conductivity of a solid sample comprising:
   a length of optical fiber;
   a temperature sensitive element held at a first end of said optical fiber, said element having temperature sensitive luminescent properties and being adapted to contact one side of the solid sample;

a radiation heat transfer means for directly supplying heat to the element;

means at a second end of the optical fiber for exciting said temperature sensitive element; and means at said second end of the optical fiber for detecting electromagnetic radiation emitted by said element to detect the temperature of the element which indicates the thermal conductivity of the solid sample.

67. The apparatus of claim 66 further comprising a heat sink adapted to contact a solid sample on a side opposite to that in contact with said element so that a steady temperature gradient may be maintained in the sample for measuring its thermal conductivity.

68. The apparatus of claim 66 wherein the thermal capacity of said element is much smaller than that of the solid sample and wherein the radiation heat transfer means is such that the heat supplied to the solid sample through the element does not significantly change the temperature of most of the solid, so that the temperature of the phosphor element is an indication of the thermal conductivity of the material of which the sample is composed.

69. The apparatus of claims 25, 30, 34, 38, 42, 48, 51, 55, 57 or 66 wherein the temperature sensitive element includes phosphor in its composition.

70. The apparatus of claim 69 further comprising means for detecting the intensities of radiation at two distinct wavelengths from the phosphor in said element to determine the temperature of the temperature sensitive element.

71. The apparatus of claim 69 further comprising means for detecting the luminescent response of the phosphor in said element over time to determine the temperature of the temperature sensitive element.

72. The apparatus of claim 71, wherein said luminescent response detecting means detects a parameter related to the luminescent decay time of the phorphor.

73. The apparatus of claims 25, 30, 34, 42, 48, 51, 55, 57 or 66 wherein the temperature sensitive element includes phosphor in its composition and wherein said radiation heat transfer means comprises:

an optical filter that absorbs infrared light but transmits light emitted by the phosphor upon excitation, said filter placed between said first end and the element and in heat conductive relationship with the element; and infrared light source for supplying infrared light to said second end which is then transmitted by the optic fiber to its first end for heating the element by heating the optical filter.

74. The apparatus of claims 30, 34, 38, 42, 48, 51, 55, 66 or 68 wherein said element includes phosphor in its composition and wherein said means for exciting said temperature sensitive element comprises a source of ultraviolet light.

75. The apparatus of claim 74, wherein said radiation heat transfer means comprises an infrared light source, said apparatus further comprising four additional lengths of optical fibers in optical communication with said length of optical fiber, the four additional lengths of optical fibers being so spatially oriented that a first additional optical fiber is used to transmit ultraviolet or visible light from the exciting means to said element, a second additional optical fiber transmits infrared light from the infrared light source to said optical filter, a third and a fourth additional optical fiber for transmitting the electromagnetic transmission from said element to detectors for detecting the intensities of radiation at two distinct wavelengths from the phosphor in said element.

76. A method for measuring the thermal conductivity of a solid sample with an element having temperature sensitive luminescent properties, said method comprising:

contacting one side of the solid sample with the element;

directly supplying heat to the element;

exciting said temperature sensitive element to luminescence; and detecting the electromagnetic radiation emitted by said element to detect the temperature of the element, said temperature being an indication of the thermal conductivity of the solid sample.

77. A method for improving the accuracy of temperature measurement wherein the measurement apparatus comprises a temperature probe housing, a temperature sensitive element held at the probe tip of said housing and means for determining the temperature of said element when said element is held in contact with a sample the temperature of which is to be measured, said method comprising:

determining the approximate temperature of the sample;

directly heating, through radiation, the probe tip and the temperature sensitive element to a temperature substantially equal to the approximate temperature of the sample to reduce the heat transfer between the probe tip and the element when they are placed in contact; and bringing said element into contact with the sample and measuring the temperature of the sample.

78. The probe apparatus of claim 25 further comprises means at the second end of the optic fiber for exciting said temperature sensitive element.

79. The apparatus of claim 57 wherein said element includes phosphor in its composition and wherein said means for exciting said temperature sensitive element comprises a source of ultraviolet light.

* * * * *

UNITED STATES PATENT AND TRADEMARK OFFICE
CERTIFICATE OF CORRECTION

PATENT NO. : 4,621,929

DATED : Nov. 11, 1986

INVENTOR(S) : Phillips

Page 1 of 2

It is certified that error appears in the above-identified patent and that said Letters Patent is hereby corrected as shown below:

Col. 20, line 30: "optic" should be --optical--;
Col. 21, line 6: insert --by radiation-- after "element";
Col. 21, line 49: "vortic" should be --vortex--;
Col. 21, line 64: insert --by radiation-- after "element";
Col. 22, line 37: "or" should be --of--;
Col. 23, line 3: insert --by radiation-- after "heat";
Col. 23, line 55: insert --by radiation-- after "element";
Col. 24, line 24: insert --radiation-- before "heat";
Col. 24, line 64: insert --by radiation-- after "element";
Col. 25, line 11: insert --through radiation-- after "state";
Col. 25, line 26: insert --through radiation-- after "state";
Col. 27, line 40: "phorphor" should be --phosphor--;
Col. 27, line 52: "optic" should be --optical--;
Col. 27, line 55: "68" should be --78--;

UNITED STATES PATENT AND TRADEMARK OFFICE
CERTIFICATE OF CORRECTION

PATENT NO. : 4,621,929  
DATED : Nov. 11, 1986  
INVENTOR(S) : Phillips

Page 2 of 2

It is certified that error appears in the above-identified patent and that said Letters Patent is hereby corrected as shown below:

Col. 28, line 24: insert --by radiation-- after "element", and
Col. 28, lines 49-50: "comprises" should be --comprising--.

Signed and Sealed this

Tenth Day of March, 1987

Attest:

DONALD J. QUIGG

Attesting Officer

Commissioner of Patents and Trademarks